United States Patent
Coller et al.

(10) Patent No.: US 10,137,187 B2
(45) Date of Patent: Nov. 27, 2018

(54) RECOMBINANT SUBUNIT DENGUE VIRUS VACCINE

(71) Applicant: Merck Sharp & Dohme Corp., Rahway, NJ (US)

(72) Inventors: Beth-Ann Griswold Coller, Kaneohe, HI (US); Vidya B. Pai, Jr., Rockville, MD (US); D. Elliot Parks, Del Mar, CA (US); Michele Yelmene, Del Mar, CA (US); Andrew J. Bett, Lansdale, PA (US); Timothy Martyak, Aiea, HI (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/861,425

(22) Filed: Sep. 22, 2015

(65) Prior Publication Data

US 2016/0074502 A1 Mar. 17, 2016

Related U.S. Application Data

(62) Division of application No. 13/881,423, filed as application No. PCT/US2011/058026 on Oct. 27, 2011, now Pat. No. 9,198,964.

(60) Provisional application No. 61/408,310, filed on Oct. 29, 2010.

(51) Int. Cl.
*A61K 39/12* (2006.01)
*C12N 7/00* (2006.01)
*A61K 39/00* (2006.01)

(52) U.S. Cl.
CPC .............. *A61K 39/12* (2013.01); *C12N 7/00* (2013.01); *A61K 2039/545* (2013.01); *A61K 2039/55505* (2013.01); *A61K 2039/55577* (2013.01); *A61K 2039/57* (2013.01); *A61K 2039/70* (2013.01); *C12N 2770/24134* (2013.01); *C12N 2770/24171* (2013.01)

(58) Field of Classification Search
CPC .............. A61K 39/12; A61K 2039/545; C12N 2770/24171; C12N 2770/24134
See application file for complete search history.

(56) References Cited

U.S. PATENT DOCUMENTS 7,718,357 B2 5/2010 Guy et al.

FOREIGN PATENT DOCUMENTS

TW 200813228 A 3/2008
WO WO2012154202 A1 11/2012

OTHER PUBLICATIONS

Clements, D. E., et al., 2010, Development of a recombinant tetravalent dengue virus vaccine: Immunogenicity and efficacy studies in mice and monkeys, Vaccine 28:2705-2715 (available online Jan. 22, 2010).*
Rothman, A. L., 2011, Immunity to dengue virus: a tale of original antigenic sin and tropical cytokine storms, Nat. Rev. Immunol. 11:532-543.*
Thomas, S. J., 2011, The necessity and quandaries of dengue vaccine development, J. Infect. Dis. 203:299-303.*
Wallace, D., et al., 2013, Challenges in the clinical development of a dengue vaccine, Curr. Opin. Virol. 3:352-356.*
Sariol, C. A., and L. J. White, 2014, Utility, limitations, and future of non-human primates for dengue research and vaccine development, Front. Immunol. 5(00452):1-15.*
Srikiatkhachorn, A., and I.-K. Yoon, 2016 (published online Nov. 2015), Immune correlates for dengue vaccine development, Exp. Rev. Vaccines 15(4):455-465.*
Thomas, S. J., and A. L. Rothman, 2015, Trials and tribulations on the path to developing a dengue vaccine, Am. J. Prev. Med. 49(6S4):S334-S344.*
Blaney, Recombinant, Live-Attenuated Tetravalent Dengue Virus Vaccine Formulations induce a Balanced, Broad, and Protective Neutralizing Antibody Response against each of the four serotypes in Rhesus Monkeys, J. Virol., 2005, 5516-5528, 79(9).
Kurane; Virus (Japanese Journal), 2002, 15-20, 52(1) [accompanied by partial English translation].

* cited by examiner

*Primary Examiner* — Jeffrey Parkin
(74) *Attorney, Agent, or Firm* — Matthew A. Leff; Laura M. Ginkel

(57) ABSTRACT

The present invention provides dengue virus vaccines and immunogenic compositions for administration to human subjects. The vaccine compositions of the present invention comprise recombinantly produced monomeric and/or dimeric forms of truncated dengue virus envelope glycoprotein that, when formulated together with an adjuvant and a pharmaceutically acceptable carrier, induce balanced tetravalent immune responses. In preferred embodiments of the compositions described herein, the DEN4 protein component is a dimeric form of DEN4. The compositions are designed to be acceptable for use in the general population, including immunosuppressed, immunocompromised, and immunosenescent individuals. Also provided herein are methods of inducing a protective immune response in a human patient population by administering the compositions described herein to the patients.

9 Claims, 2 Drawing Sheets

Specification includes a Sequence Listing.

| Group | Animal ID | Challenge Virus | Post Challenge Bleed Day | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| 1 | CT34 | DENV1 | – | – | – | – | – | – | – | – | – | – | – |
| | CR14 | | – | – | – | – | – | – | – | – | – | – | – |
| | CN96 | | – | – | – | – | – | – | – | – | – | – | – |
| | CN94 | DENV2 | – | – | – | – | – | – | – | – | – | – | – |
| | CM80 | | – | – | – | – | – | – | – | – | – | – | – |
| | CM50 | | – | – | – | – | – | – | – | – | – | – | – |
| | CL84 | DENV3 | – | – | – | – | – | – | – | – | – | – | – |
| | CL47 | | – | – | – | – | – | – | – | – | – | – | – |
| | CL25 | | – | – | – | – | – | – | – | – | – | – | – |
| | CI27 | DENV4 | – | – | – | – | – | – | – | – | – | – | – |
| | CH97 | | – | – | – | – | – | – | – | – | – | – | – |
| | CN32 | | – | – | – | – | – | – | – | – | – | – | – |
| 2 | DD36 | DENV1 | – | – | – | – | – | – | – | – | <50 | – | – |
| | CV43 | | – | – | – | – | – | – | – | – | – | – | – |
| | CV09 | | – | – | – | – | – | – | – | – | – | – | – |
| | CT32 | DENV2 | – | – | – | – | – | – | – | – | – | – | – |
| | CT04 | | – | – | – | – | – | – | – | – | – | – | – |
| | CP26 | | – | – | – | – | – | – | – | – | – | – | – |
| | CN39 | DENV3 | – | – | – | – | – | – | – | – | – | – | – |
| | CN36 | | – | – | – | – | – | – | – | – | – | – | – |
| | CM48 | | – | – | – | – | – | – | – | – | – | – | – |
| | CL29 | DENV4 | – | – | – | – | – | – | – | – | – | – | – |
| | CJ28 | | – | – | – | – | – | – | – | – | – | – | – |
| | CI20 | | – | – | – | – | – | – | – | – | – | – | – |
| 3 | SBR17 | DENV1 | – | – | <50 | <50 | <50 | <50 | 250 | 150 | – | – | – |
| | SBR35 | | – | – | – | <50 | <50 | 75 | 100 | – | – | – | – |
| | PH0941 | | – | <50 | – | <50 | – | 75 | <50 | – | – | – | – |
| | PH0913 | DENV2 | – | – | – | – | – | 50 | – | – | – | – | – |
| | SBR45 | | – | – | – | – | – | – | – | – | <50 | – | <50 |
| | N316 | | – | – | – | – | – | 50 | 50 | <50 | 50 | 50 | – |
| | CN41 | DENV3 | – | 50 | <50 | – | <50 | – | – | – | – | – | – |
| | CJ78 | | <50 | <50 | <50 | – | – | – | – | – | – | – | – |
| | 94E117 | | 50 | 50 | – | <50 | <50 | – | – | – | – | – | – |
| | FPD | DENV4 | – | – | – | – | – | – | – | – | – | – | – |
| | DDB/636 | | – | – | – | – | – | 50 | 50 | – | – | – | – |
| | CH54 | | – | – | – | – | – | <50 | 225 | <50 | <50 | – | – |

FIG.2

RECOMBINANT SUBUNIT DENGUE VIRUS VACCINE

CROSS-REFERENCE TO RELATED APPLICATIONS

This application is a divisional of pending U.S. application Ser. No. 13/881,423, filed Apr. 25, 2013, which is a § 371 National Stage Application of PCT/US2011/058026, having an international filing date of Oct. 27, 2011, which claims the benefit of U.S. Provisional Application No. 61/408,310, filed Oct. 29, 2010, the contents of which are herein incorporated by reference in their entirety.

STATEMENT REGARDING FEDERALLY SPONSORED RESEARCH

The invention was supported, in part, by U.S. Government grants numbered 5UO1 AI056410-03, and 1UC1 AI062481 (NIH), and W81XWH-06-2-0035 (DOD). The U.S. Government has certain rights in this invention.

REFERENCE TO SEQUENCE LISTING SUBMITTED ELECTRONICALLY

The sequence listing of the present application is submitted electronically via EFS-Web as an ASCII formatted sequence listing with a file name "MRLIFD00058USDIV_SEQLIST.TXT", with a creation date of Dec. 1, 2015, and a size of 29.3 kilobytes. This sequence listing submitted via EFS-Web is part of the specification and is herein incorporated by reference in its entirety.

FIELD OF THE INVENTION

The invention relates to compositions that elicit an immunological response against dengue virus infections, useful for the prevention and/or treatment of dengue virus infections in human subjects, and the clinical manifestations thereof.

BACKGROUND OF THE INVENTION

The family Flaviviridae includes the prototype yellow fever virus (YF), the four serotypes of dengue virus (DEN-1, DEN-2, DEN-3, and DEN-4), Japanese encephalitis virus (JE), tick-borne encephalitis virus (TBE), West Nile virus (WN), Saint Louis encephalitis virus (SLE), and about 70 other disease causing viruses. Flaviviruses are small, enveloped viruses containing a single, positive-strand RNA genome. Ten gene products are encoded by a single open reading frame and are translated as a polyprotein organized in the order: capsid (C), "preMembrane" (prM, which is processed to "Membrane" (M) just prior to virion release from the cell), "envelope" (E), followed by non-structural (NS) proteins NS1, NS2a, NS2b, NS3, NS4a, NS4b and NS5 (reviewed in Chambers, T. J. et al., *Annual Rev Microbiol* (1990) 44:649-688; Henchal, E. A. and Putnak, J. R., *Clin Microbiol Rev.* (1990) 3:376-396). Individual flaviviral proteins are then produced through precise processing events mediated by host as well as virally encoded proteases.

The envelope of flaviviruses is derived from the host cell membrane and contains the virally-encoded membrane anchored membrane (M) and envelope (E) glycoproteins. The E glycoprotein is the largest viral structural protein and contains functional domains responsible for cell surface attachment and intra-endosomal fusion activities. It is also a major target of the host immune system, inducing the production of virus neutralizing antibodies, which are associated with protective immunity.

Dengue viruses are transmitted to man by mosquitoes of the genus *Aedes*, primarily *A. aegypti* and *A. albopictus*. Infection by dengue viruses leads to a diverse clinical picture ranging from an inapparent or mild febrile illness, through classical dengue fever (DF) characterized by high fever, headache, joint and muscle pain, rash, lymphadenopathy and leucopenia (Gibbons, R. V. and D. W. Vaughn, *British Medical Journal* (2002) 324:1563-1566), to a more severe form of infection more common in children, dengue hemorrhagic fever/dengue shock syndrome (DHF/DSS), marked by vascular permeability and/or severe hemorrhagic manifestations ranging from the presence of petechiae and ecchymosis to spontaneous severe hemorrhage and profound shock which may, if untreated, result in death. Without diagnosis and prompt medical intervention, the sudden onset and rapid progression of DHF/DSS can be fatal.

Dengue viruses are the most significant group of arthropod-transmitted viruses in terms of global morbidity and mortality with an estimated one hundred million cases of dengue fever occurring annually including 250,000 to 500,000 cases of DHF/DSS (Gubler, D. J., *Clin. Microbiol. Rev.* (1998) 11:480-496; Gibbons, supra). With the global increase in population, urbanization of the population especially throughout the tropics, and the lack of sustained mosquito control measures, the mosquito vectors of dengue have expanded their distribution throughout the tropics, subtropics, and some temperate areas, bringing the risk of dengue infection to over half the world's population. Modern jet travel and human emigration have facilitated global distribution of dengue serotypes, such that multiple serotypes of dengue are now endemic in many regions. There has been an increase in the frequency of dengue epidemics and the incidence of DHF/DSS in the last 20 or more years. For example, in Southeast Asia, DHF/DSS is a leading cause of hospitalization and death among children (Gubler, supra; Gibbons and Vaughn, supra).

To date, the development of flavivirus vaccines has been met with mixed success. There are four basic approaches that have been implemented in an effort to produce vaccine candidates to protect against disease causes by flaviviruses: live-attenuated, inactivated whole virus, recombinant subunit protein, and DNA-based vaccines. A live-attenuated vaccine for Yellow Fever virus has been available for decades. The use of inactivated whole virus vaccines has been demonstrated for TBE and JE viruses.

Despite the successes of the YF, JE, and TBE vaccines highlighted above, the use of live-attenuated virus and inactivated virus methods to develop vaccines for dengue virus has been met with significant challenges. There are four serotypes of dengue virus (DEN1, DEN2, DEN3, and DEN4) and strains of each serotype are found circulating throughout the dengue endemic regions of the world. Natural infection confers long lasting immunity to the infecting serotype but not to other dengue serotypes. The more severe forms of the disease (DHF/DSS) occur most often after secondary dengue infection, when infection with one serotype of dengue virus is followed by a second infection with another serotype. The more frequent association of DHF and DSS with secondary dengue infection has been hypothesized to be due to non-neutralizing antibodies induced by infection with one virus type enhancing infectivity of a second dengue virus type (antibody-dependent enhancement—ADE). This concept has important implications for vaccine development, as an effective dengue vaccine must simultaneously induce balanced specific neutralizing antibodies and specific memory cells against all four dengue serotypes (Halstead and Deen, 2002). This has proven to be a major problem in dengue vaccine development.

To date, the majority of the vaccines tested clinically are live, attenuated vaccines, which present safety concerns common to all live viral vaccines given to healthy subjects. Under-attenuation of the virus may result in virus-related adverse events, whereas over-attenuation may abrogate vaccine efficacy. Also, reversion to wild type or mutation to increased virulence (or decreased efficacy) may occur. Moreover, even if properly attenuated, live viral vaccines are contraindicated for specific patient populations, such as immune deficient or immune suppressed patients, as well as particular segments of the normal population, such as pregnant women, infants, or elderly individuals.

Further issues with live attenuated virus approaches for dengue include the challenges associated with combination of four independently replicating viruses in a tetravalent vaccine. Issues with interference have plagued all tetravalent formulations tested to date and have resulted in unbalanced tetravalent immunity and the requirement for multiple doses administered at an extended interval (e.g. 0, 6, 12 months). This is less than ideal and could present safety issues for individuals who have been partially immunized and become exposed to wild type virus as these individuals may be at higher risk of exacerbated disease (e.g. dengue hemorrhagic fever).

Ivy et al. (U.S. Pat. No. 6,432,411) disclose a tetravalent subunit vaccine comprising DEN1-4 80% E (equivalent to amino acids 1-395 of the DEN-2 envelope polypeptide) proteins. Ivy et al, supra, also report compositions comprising DEN 1-4 80% E and ISCOMATRIX® adjuvant. There remains a need; however, for stable, tetravalent vaccines that can induce a balanced immune response against all four dengue serotypes.

SUMMARY OF THE INVENTION

The present invention provides vaccines and immunogenic compositions for use in human patient populations for the prevention and/or treatment of disease associated with dengue virus infections. The vaccines are formed by the combination of recombinant subunit protein(s) derived from dengue virus envelope protein(s) and an adjuvant. The dengue virus vaccines of the present invention are designed to induce balanced, protective, tetravalent immune responses against DEN1, DEN2, DEN3, and DEN4, while providing an acceptable safety profile.

The unique vaccine formulation depends upon novel, properly folded recombinant envelope subunit proteins ("dengue 80E" or "DEN-80E" or "DEN1-80E" or "DEN2-80E" or "DEN3-80E" or "DEN4-80E" or "DEN4-80EZip") combined with adjuvants to produce the vaccine formulations. The unique combination in varying ratios of monomeric and/or dimeric forms of the recombinant envelope proteins of the formulation are designed specifically to address the need for balanced tetravalent responses. The vaccines are designed to induce relevant, balanced, tetravalent protective immune responses, such as virus neutralizing antibody in healthy human volunteers and to maintain an acceptable safety profile for administration to healthy and immunocompromised individuals. An additional advantage of the vaccine compositions described herein is that they do not contain significant quantities of the pre-membrane (prM) protein, potentially minimizing risk of ADE which has recently been linked to anti-prM antibodies (Dejnirattisai et al., Science 328:745-748 (2010); Rodenhuis-Zybert et al., PLos Pathogens 6:1-9 (2010)). The 80E proteins are expressed co-translationally with prM, but the polyprotein is cleaved as it transits the secretory pathway at the prM-E junction by host cell signalase releasing the 80E component into the culture medium for purification (Clements et al., 2010 Vaccine 28:2705).

Other aspects of this invention include use of therapeutically effective amounts of the vaccines in an acceptable carrier as an immunoprophylactic against disease caused by dengue virus infection and use of the therapeutically effective amount of the vaccines in an acceptable carrier as a pharmaceutical composition.

As used throughout the specification and in the appended claims, the singular forms "a," "an," and "the" include the plural reference unless the context clearly dictates otherwise.

As used throughout the specification and appended claims, the following definitions and abbreviations apply:

The term "treatment" refers to both therapeutic treatment and prophylactic or preventative measures. Individuals in need of treatment include those already with the dengue infection, whether or not manifesting any clinical symptoms, as well as those at risk of being infected with dengue, i.e. those subjects/patients in which dengue infection and/or the clinical manifestations thereof are to be prevented. Treatment of a patient with the dengue vaccines of the invention includes one or more of the following: inducing/increasing an immune response against dengue in the patient, preventing, ameliorating, abrogating, or reducing the likelihood of the clinical manifestations of dengue in patients who have been infected with dengue, preventing or reducing the likelihood of developing dengue fever, DHF, or DSS and/or other disease or complication associated with dengue infection, reducing the severity or duration of the clinical symptoms of dengue infection and/or other disease or complication associated with the dengue, and preventing or reducing the likelihood of dengue infection.

The term "therapeutically effective amount" means sufficient vaccine composition is introduced to a patient to produce a desired effect, including, but not limited to: inducing/increasing an immune response against dengue in the patient, preventing or reducing the likelihood of dengue infection or dengue recurrent infection, preventing, ameliorating or abrogating the clinical manifestations of dengue infection in patients who have been infected with dengue, preventing dengue fever, DHF and/or DSS, reducing the severity or duration of disease associated with dengue. One skilled in the art recognizes that this level may vary.

The term "immune response" refers to a cell-mediated (T-cell) immune response and/or an antibody (B-cell) response.

The term "patient" refers to any human being that is to receive the dengue vaccine/immunogenic compositions described herein, including both immunocompetent and immunocompromised individuals. As defined herein, a "patient" includes those already infected with dengue, either through natural infection or vaccination or those that may subsequently be exposed.

"MAA" means Merck aluminum adjuvant. MAA is an amorphous aluminum hydroxyphosphate sulfate adjuvant. The term "MAA" is used interchangeably herein with the term "amorphous aluminum hydroxyphosphate sulfate" or "AAHS."

An "ISCOM-like adjuvant" is an adjuvant comprising an immune stimulating complex (ISCOM), which is comprised of a saponin, cholesterol, and a phospholipid, which together form a characteristic caged-like particle, having a unique spherical, caged-like structure that contributes to its function (for review, see Barr and Mitchell, *Immunology and Cell Biology* 74: 8-25 (1996)). This term includes both ISCOM adjuvants, which are produced with an antigen and comprise antigen within the ISCOM particle and ISCOM matrix adjuvants, which are hollow ISCOM-type adjuvants that are produced without antigen. In preferred embodiments of the compositions and methods provided herein, the ISCOM-type adjuvant is an ISCOM matrix particle adjuvant, such as ISCOMATRIX®, which is manufactured without antigen (ISCOM® and ISCOMATRIX® are the registered trademarks of CSL Limited, Parkville, Australia).

BRIEF DESCRIPTION OF THE DRAWINGS

FIG. 2 shows results of a tetravalent dengue rhesus macaque challenge study: post challenge quantitative viremia assessment by direct plaque assay of monkey serum on Vero cells, as described in Example 6.

DETAILED DESCRIPTION OF THE INVENTION

Figure 1A:
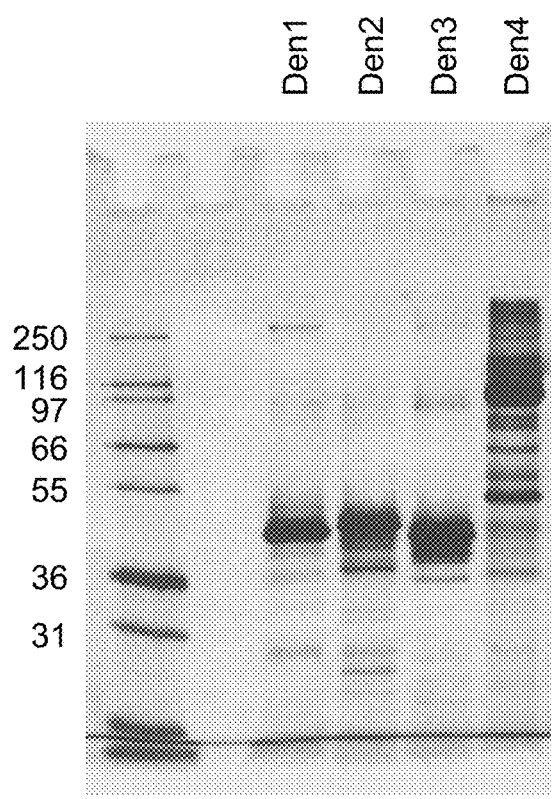
FIGS. 1A-B show a silver stained sodium dodecyl sulphate-polyacrylamide gel electrophoresis (SDS-PAGE) gel (1A) and Western blot (1B) of purified cGMP grade DEN1-80E, DEN2-80E, DEN3-80E and DEN4-80EZip (1 μg of each sample). All samples were run under non-reducing conditions on 10% gels. The Western blot was developed using a mouse monoclonal antibody (4G2) which recognizes all dengue viruses. The sizes of the molecular weight markers (in kD) are indicated to the left of the gel and blot.

As described above, several attempts at the development of a dengue vaccine for human use have been made, but so far, these attempts have been plagued by issues with safety and/or efficacy. To that end, the present invention provides compositions that are useful for the prevention and/or treatment of dengue virus infections in human subjects, and/or the clinical manifestations thereof.

Many previous efforts have been directed at the development of human dengue vaccines that are both safe and sufficiently immunogenic (e.g. capable of inducing balanced tetravalent responses in immunized individuals). Despite these efforts, no dengue virus vaccines for human use, that fully meet these conditions, have been established to date. Therefore, the technical problem to be solved by the invention is the discovery of dengue virus vaccines that satisfy two major conditions; the ability to (1) induce balanced, tetravalent protective immune responses in vaccinated individuals (human subjects), and (2) maintain an exceptional safety profile in human subjects including infants, elderly and immunocompromised. This represents a significant challenge in dengue virus vaccine development, and to date no vaccine formulation has been shown to adequately address all aspects of this technical problem. There is a high, unmet and growing demand, for a solution as the prevalence of dengue viral infections increase.

All flavivirus envelope proteins share significant homology. Antibodies directed against epitopes contained within all three external domains of the envelope protein are capable of viral neutralization, i.e., the inhibition of virus infection of susceptible cells in vitro. A high titer of viral neutralizing antibodies is generally accepted as the best in vitro correlate of in vivo protection against flaviviral infection and prevention of flavivirus induced disease (Markoff *Vaccine* (2000) 18:26-32; Ben-Nathan et al., *J. Inf. Diseases* (2003) 188:5-12; Kreil et al., *J. Virol.* (1998) 72:3076-3081; Beasley et al., *Vaccine* (2004) 22:3722-26). Therefore, a vaccine that induces high titer dengue virus neutralizing responses will likely protect vaccinees against disease induced by dengue viruses.

The more frequent association of DHF and DSS with secondary dengue infection is hypothesized to be due to the presence of cross reactive, non-neutralizing, antibodies resulting from the first infection, which up regulate replication of the second infecting serotype by promoting infection of Fc receptor bearing cells such as monocytes/macrophages by the Fc-receptor-mediated route (ADE; Halstead 1988; Halstead 1989). Alternatively, a more recent hypothesis holds that through the phenomenon of "original antigenic sin" the initial immune response is directed primarily against the first infecting serotype, which allows the second infecting serotype to replicate and gain an advantage before a more specific immune response can be initiated (Mongkolsapaya et al., 2003). Regardless of mechanism, this phenomenon of enhanced secondary infection has important implications for vaccine development, as an effective dengue vaccine must simultaneously induce balanced specific neutralizing antibodies and specific memory cells against all four dengue serotypes (Halstead and Deen, 2002). This has proven to be a major problem in dengue vaccine development.

To demonstrate how this problem has caused issues in dengue vaccine development a review of efforts conducted to date is useful. A significant amount of effort has been invested in developing candidate live-attenuated dengue vaccine strains; however, many of the strains tested have proven unsatisfactory and interference between viral serotypes has proven very challenging. Two development programs using classically attenuated viruses progressed to Phase 2 clinical testing, but were stalled or halted in Phase 2 due to interference and/or production issues.

As an alternative to traditional live-attenuated methods to develop flavivirus vaccines, recombinant chimeric methods have been utilized. This method utilizes a known attenuated strain as a base and the appropriate genes (prM and E for flaviviruses) from a related virus of interest are substituted for the equivalent genes of the base virus. One approach that has been used for WN and dengue vaccine development is use of an intertypic chimeric based on an attenuated DEN-4 strain (Bray, M. et al., *J. Virol.* (1996) 70:4162-4166; Chen, W., et al., *J. Virol.* (1995) 69:5186-5190; Bray, M. and Lai, C.-J., *Proc. Natl. Acad. Sci. USA* (1991) 88:10342-10346; Lai, C. J. et al., *Clin. Diagn. Virol.* (1998) 10:173-179). Another approach has been the use of the YF 17D attenuated strain as a base to develop recombinant chimeric vaccines for JE virus, DEN viruses, and WN virus (Guy, B. et al. Vaccine (2011), doi: 10.1016/j.vaccine.2011.06.094; Lai, C. J. and Monath T. P. *Adv Virus Res* (2003) 61:469-509; Monath et al. *Proc. Natl. Acad. Sci. USA* (2006) 103:6694). While the use of live-attenuated chimeric methods has advantages over traditional live-attenuated methods, the chimeric methods are still plagued by difficulties faced in developing properly attenuated strains and in achieving balanced, tetravalent responses against dengue viruses.

Currently there are commercially available vaccines produced for JE and TBE utilizing whole inactivated virus methods. As with live-attenuated virus methods, the use of inactivated virus methods for certain flaviviruses has not guaranteed success with other flaviviruses. For example, efforts to develop inactivated DEN vaccines have met with limited success. Primarily these approaches have been limited by the inability to obtain adequate viral yields from cell culture systems. Virus yields from insect cells such as C6/36 cells are generally in the range of $10^4$ to $10^5$ pfu/ml, well below the levels necessary to generate a cost-effective inactivated virus vaccine. Yields from mammalian cells including LLC-MK2 and Vero cells are higher, but the peak yields, approximately $10^6$ pfu/ml from a unique Vero cell line, are still lower than necessary to achieve a truly cost-effective vaccine product. Low yields may further impact the ability to induce balanced tetravalent responses.

The use of naked DNA methods has also been evaluated in an effort to develop non-replicating flavivirus vaccines for DEN, JE, TBE and WN (Porter et al, 1998; Raviprakash et al, 2000; Konishi et al, 1998; Chang et al, 2000; Schmaljohn et al, 1997; Aberle et al, 1999; Davis et al, 2001). The DNA method offers advantages in ease of production, use of defined sequences, potential to elicit both humoral and cellular immunity due to the expression of antigens in vivo. Despite these advantages, the ability to induce consistent and robust immune response continues to be a major hurdle to this approach. While there has been some success inducing relevant protective immune responses in animal models (Davis et al, 2001), the ability to induce these responses in humans is not yet established. Additionally, DNA vaccines face additional regulatory scrutiny due to concerns about integration of plasmid sequences in the host genome and the potential of generating auto-antibodies to double stranded DNA.

The use of recombinant subunit proteins for flavivirus vaccine development is another example of a non-replicating virus approach. This approach offers advantages in production of well defined products and the potential to elicit specific immune responses. While the potential to generate relevant and robust immune responses exist, there are challenges associated with use of recombinant subunits This is due to both the quality of the proteins (native-like structure) and the need for adjuvants in eliciting the desired immune responses. Recombinant subunit vaccines have a long history of safety and protective efficacy illustrated most effectively by the recombinant subunit Hepatitis B vaccines (e.g. RECOMBIVAX HB® (Merck Sharp & Dohme Corp., Whitehouse Station, N.J.) and ENGERIX B® (GlaxoSmithKline Biologicals SA Corp., Belgium) and more recently by the human papilloma virus vaccines (e.g. GARDASIL® (Merck Sharp & Dohme Corp.) and CERVARIX® (GlaxoSmithKline Biologicals SA Corp.). The fact that there is no replicating virus present at any time during production helps assure that there is very limited risk associated to administration of the subunit vaccine to healthy or immunocompromised individuals in a prophylactic setting. Moreover, the Hepatitis B and human papillomavirus vaccines have been shown to be highly immunogenic and efficacious.

The expression of recombinant flavivirus proteins has focused on the structural proteins C, prM and E and the non-structural protein NS1. The E protein has been the subject of most efforts as this protein is exposed on the surface of the virus and is involved in important biological aspects of the virus and is the target of neutralizing antibodies in infected hosts (Chambers, supra; Mason, P. W., J. Gen Virol (1989) 70:2037-2048). Furthermore, monoclonal antibodies directed against purified flavivirus E proteins are neutralizing in vitro and some have been shown to confer passive protection in vivo (Henchal, E. A. et al., Am. J. Trop. Med. Hyg. (1985) 34:162-169; Heinz, F. X. et al., Virology (1983) 130:485-501; Kimura-Kiroda, J. and Yasui, K., J. Immunol. (1988) 141:3606-3610; Trirawatanapong, T. et al., Gene (1992) 116:139-150).

Towards the goal of producing recombinant flavivirus proteins for use in vaccines a variety of expression systems have been utilized such as E. coli, yeast and baculovirus. These attempts have been plagued by low yields, improper processing of the flavivirus proteins, and moderate to poor immunogenicity (Eckels and Putnak, 2003). There is a need to maintain the native-like structure of the E protein in order for the recombinant proteins to serve as potent immunogens. The ability to produce recombinant E proteins with native-like structure is highly dependent on the expression system utilized. U.S. Pat. No. 6,165,477 discloses the process for expression of DEN E protein subunits in yeast cells. The E subunits expressed in yeast cells demonstrated improved structure over bacterial systems, but still faced problems with hyper-glycosylation and yields.

In more recent studies, it has been established that the use of stably transformed insect cells to express truncated forms of the E protein results in products that maintain native-like structure as determined by X-ray crystallography (Modis et al, 2003; Modis et al, 2005; and Zhang et al, 2004). The use of the stably transformed insect cell system has resulted in successful expression of truncated recombinant Flavivirus E proteins, such as DEN serotypes 1-4, JE, TBE and WN. U.S. Pat. No. 6,136,561 discloses the process for expression of DEN, JE, TBE and YF E subunit proteins in stably transformed insect cells. Ivy et al. (U.S. Pat. No. 6,432,411) disclose the utility of flavivirus E subunit proteins (equivalent to amino acids 1-395 of the DEN-2 envelope polypeptide) expressed in stably transformed insect cells as candidate vaccines when combined with saponin containing iscom-like structures. Ivy et al. further report a tetravalent subunit vaccine comprising 80% E proteins from all four DEN types (DEN 1-4), as well as compositions comprising DEN 1-4 80% E and ISCOMATRIX® adjuvant. A small pilot study analyzing the immunogenicity and protective efficacy of this tetravalent vaccine in monkeys was performed (Clements et al., Vaccine 28: 2705-15 (2010); Coller et al. Vaccine 29: 7267-75 (2011)). The vaccine was said to induce neutralizing antibodies and protective immunity against more than one dengue type. U.S. Pat. No. 6,749,857 discloses the expression of dimeric forms of the truncated dengue envelope proteins such as the DEN4-80EZip described in the current application. U.S. Pat. No. 6,416,763 describes the benefit of including non-structural protein 1 (NS1) produced by stably transformed insect cell lines in a recombinant E-based vaccine formulation. These patents demonstrate the utility of the flavivirus subunits expressed from stably transformed insect cells when combined with the saponin containing iscom-like structures in animal models. However, these patents do not address or predict a vaccine formulation based solely on E formulated with an adjuvant that has demonstrated immunogenicity in human subjects. Many vaccine candidates have demonstrated potential efficacy in animal models but failed to make the successful transition to human use.

In general, the use of non-replicating virus vaccine approaches such as inactivated virus, recombinant subunit protein and DNA have several advantages over the live-attenuated virus vaccine approaches. Primarily these advantages are related to safety as no live virus is delivered to subjects. Other advantages include the ability to accelerate dosing schedules compared to live attenuated viruses and the ability to modulate and balance immune responses by adjusting dosage and adjuvantation.

In the development of flavivirus vaccines for humans it has been difficult to predict safety and immunogenicity of candidate vaccines in human subjects based on preclinical data in animal models. This has proved challenging for many of the live-attenuated virus vaccine candidates that have advanced to human clinical trials. The most glaring example of a complete failure was the safety profile exhibited by a cloned dengue virus type 3 isolate which displayed a very attractive safety profile in non-human primates, but which induced dengue fever in vaccine recipients in Hong Kong (Sanchez et al., *FEMS Immunol. Med. Microbiol.* (2006) 24:4914-26). This challenge may be decreased by use of non-replicating virus vaccines which do not require the same level of virus/host interactions in order to achieve vaccine efficacy as replicating virus vaccines. However, there are numerous examples of non-replicating virus vaccine candidates which have shown good safety and protective efficacy in preclinical models, which failed to function as safe and effective vaccines in humans (e.g. inactivated RSV vaccine; Murphy et al., *J. Clin. Microbiol.* (1986) 24:197-202). Thus, there can be multiple challenges associated to developing safe and effective vaccines for flaviviruses and development often requires years of trial and error. Furthermore, preclinical studies based on animal models may not be predictive of vaccine performance in human subjects; and therefore, human data is critical in demonstrating a candidate vaccine's potential.

While there are numerous investigational dengue vaccines in various stages of preclinical research and development, only six vaccine candidates have proceeded to human clinical trials. The six vaccines that have been tested in clinical studies are: (1) live, attenuated dengue serotype 4 chimeras (e.g. Durbin et al. 2006, Human Vaccines 2:167; Blaney et al., 2005, J. Virol. 79:5516); (2) live, attenuated Yellow Fever-dengue chimeras (Chimerivax; e.g. Morrison et al., 2010, *J. Inf. Dis.* 201:370); (3) classically attenuated virus vaccines developed by the Walter Reed Army Institute of Research (e.g. Sun et al., 2009, Human Vaccines 5:33); (4) live, attenuated dengue serotype 2 chimeras (e.g. Huang et al., 2003, J. Virol. 77:11436); (5) a DNA-based vaccine expressing prM-E (Raviprakash et al., 2006, Virology 353: 166); and (6) classically attenuated virus vaccines developed by Mahidol University (e.g. Bhamarapravati et al., 1987). However, there are intrinsic difficulties and potential shortcomings associated with each of the candidate vaccines.

Further issues with live attenuated virus approaches for dengue include the challenges associated to combination of four independently replicating viruses in a tetravalent vaccine. Issues with interference have plagued all tetravalent formulations tested to date and have resulted in unbalanced tetravalent immunity and the requirement for 3 doses administered at an extended interval (e.g. 0, 6, 12 months). This is less than ideal and could present safety issues for individuals who have been partially immunized and become exposed to wild type virus as these individuals may be at higher risk of exacerbated disease (e.g. dengue hemorrhagic fever).

The final dengue vaccine that has been tested in clinical trials is a DNA vaccine. Naked DNA vaccines are unproven for any infectious disease at this time, and the issue of potential immunopathology due to the induction of an autoimmune reaction to the DNA over the long term is unresolved. No or low virus neutralizing antibodies were elicited by the vaccine formulations tested, suggesting lack of potential efficacy.

One aspect of the invention described herein provides a subunit dengue virus envelope glycoprotein (e.g. DEN1-80E, DEN2-80E, DEN3-80E, DEN4-80E, or DEN4-80EZip) that is produced and secreted using a recombinant expression system and combined with an adjuvant in a vaccine formulation (e.g. HBV-001 D1). The disclosed vaccines are effective in inducing a virus neutralizing antibody response to the homologous dengue viruses in human volunteers and have an acceptable safety profile for healthy and at-risk human subjects.

To that end, one aspect of the present invention provides an immunogenic composition comprising an effective amount of purified dengue virus envelope ("E") proteins of serotype DEN-1, DEN-2, DEN3, and DEN-4, a pharmaceutically acceptable excipient, and an effective amount of adjuvant; wherein the E proteins each constitute approximately 80% of the length of wild type E starting from amino acid residue 1 at its N-terminus, such that said E protein is secretable into growth medium when expressed recombinantly in a host cell; wherein the DEN-4 E protein is dimeric ("DEN4-80EZip"); and wherein the composition induces the production of neutralizing antibodies in human subjects. In preferred embodiments of this aspect of the invention, the E proteins in the composition described above are recombinantly produced and expressed in insect host cells. In further preferred embodiments, the E protein is recombinantly produced and expressed in *Drosophila melanogaster* Schneider 2 (S2) host cells, as described, infra.

The recombinant subunit dengue virus E proteins of the present invention are produced by means of a cell culture expression system that uses *Drosophila* Schneider 2 (S2) cells. This system has been demonstrated to produce dengue recombinant envelope proteins that maintain native-like structure (Cuzzubbo et al., *Clin. Diagn. Lab. Immunol.* (2001) 8:1150-55; Modis et al., *Proc. Natl. Acad. Sci.* (2003) 100:6986-91; Modis et al., *Nature* (2004) 427:313-9; Zhang et al., Structure (2004)12(9):1607-18). This expression system has also been shown to express other recombinant envelope proteins from other flaviviruses such as West Nile, Japanese Encephalitis, hepatitis C, and Tick Borne Encephalitis viruses. The recombinant envelope proteins are typically truncated at the C-terminus, leaving 80% of the native envelope protein ("80E"). Thus 80E is defined as approximately the first 80% of consecutive amino acids of E protein starting at amino acid 1 of its N-terminus.

The scope of the truncated 80E proteins used in the invention deletes the membrane anchor portion (approximately the last 10% of E at the carboxy end) of the protein, in other words, up to the first 90% of consecutive amino acids of E starting at amino acid 1 of its N-terminus, thus allowing it to be secreted into the extracellular medium, facilitating recovery. The truncation further deletes the "stem" portion of the E protein that links the 80E portion with the membrane anchor portion; the stem portion does not contain notable antigenic epitopes and therefore is not included in the preferred antigens, DEN1-80E, DEN2-80E, DEN3-80E, DEN4-80E, or DEN4-80EZip. More than 90%, but less than 100%, of the E protein can be cloned and secreted, i.e., the protein can be 90%+ in length, carboxy truncated, and can include a portion of the membrane spanning domain so long as the truncated E protein is secretable. "Secretable" means able to be secreted, and typically secreted, from the transformed cells in the expression system. Thus, one of skill in the art will realize that Dengue E proteins that are useful in the compositions and methods of the present invention may vary from the 80% exemplified herein, as long as the protein is secretable. In preferred embodiments of each aspect of the present invention, the DEN E proteins are about 80% in length starting from the N-terminal amino acid of the envelope protein and ending at an amino acid in the range of the $395^{th}$ to $401^{st}$ amino acid, for example, from amino acid 1 to amino acid 395 of dengue virus type 2. In alternative embodiments of each aspect of the invention, the dengue E protein may be about 75%, about 85%, about 90%, about 95%, or about 98% of the consecutive amino acids of E starting at amino acid 1 of its N-terminus. In exemplary embodiments of aspects of the invention herein, the DEN E protein is approximately 80% of consecutive amino acids of E protein starting at amino acid 1 of its N-terminus; such as DEN1-80E, as set forth in SEQ ID NO:6, DEN2-80E, as set forth in SEQ ID NO:7, DEN3-80E, as set forth in SEQ ID NO:8 and DEN4-80E, as set forth in SEQ ID NO:9.

The secreted E protein may further contain domains which facilitate dimerization, such as in the DEN4-80EZip protein, such that the immunogenicity of the recombinant protein is further enhanced. An exemplary DEN4-80EZip protein comprises an amino acid sequence as set forth in SEQ ID NO:10. By combining the dimeric and monomeric forms of the recombinant E proteins from the four dengue viruses, the immune response can be modulated such that balanced tetravalent responses are induced. When the recombinant dengue virus 80E subunit proteins are properly formulated for human use they are able to induce potent virus neutralizing antibodies in human subjects. Thus the invention provides a novel solution to a key technical problem: the production of a dengue virus vaccine which demonstrates both a high level of safety and balanced tetravalent immunogenicity in human subjects.

Adjuvants

The vaccine formulation/immunogenic compositions of the present invention include at least one adjuvant that is suitable for human use. In a preferred embodiment, the dengue 80E recombinant subunit proteins are formulated with saponin-based ("ISCOM-like") adjuvants (e.g. ISCO-MATRIX® adjuvant) and/or aluminum-based adjuvants (collectively, "alum" or "alum-based adjuvants").

Aluminum has long been shown to stimulate the immune response against co-administered antigens, primarily by stimulating a $T_H2$ response and aluminum-based adjuvants were the first adjuvants registered for human use in the United States. In addition to dengue 80E antigens as described herein, the compositions of this aspect of the present invention are adsorbed to aluminum adjuvant such as aluminum hydroxide, aluminum phosphate, or a mixture thereof. It is preferred that the aluminum adjuvant of the compositions provided herein is not in the form of an aluminum precipitate. Aluminum-precipitated vaccines may increase the immune response to a target antigen, but have been shown to be highly heterogeneous preparations and have had inconsistent results (see Lindblad E. B. *Immunology and Cell Biology* 82: 497-505 (2004)). Aluminum-adsorbed vaccines, in contrast, can be preformed in a standardized manner, which is an essential characteristic of vaccine preparations for administration into humans. Moreover, it is thought that physical adsorption of a desired antigen onto the aluminum adjuvant has an important role in adjuvant function, perhaps in part by allowing a slower clearing from the injection site or by allowing a more efficient uptake of antigen by antigen presenting cells.

Alum-based adjuvants are believed to function at least partially via a depot mechanism and the combination of the recombinant dengue 80E antigens with native-like structure and the adjuvant effect of the alum is sufficient to induce a potent immune response in vaccinated individuals, including members of the immunodeficient population.

The aluminum adjuvant of the present invention may be in the form of aluminum hydroxide $(Al(OH)_3)$, aluminum phosphate $(AlPO_4)$, aluminum hydroxyphosphate, amorphous aluminum hydroxyphosphate sulfate (AAHS) or so-called "alum" $(KAl(SO_4).12H_2O)$ (see Klein et al., Analysis of aluminum hydroxyphosphate vaccine adjuvants by (27) Al MAS NMR., *J. Pharm. Sci.* 89(3): 311-21 (2000)). In exemplary embodiments of the invention provided herein, the aluminum adjuvant is aluminum hydroxide In some embodiments of the invention, the aluminum adjuvant is in the form of AAHS (referred to interchangeably herein as Merck aluminum adjuvant (MAA)). MAA carries zero charge at neutral pH, while AlOH carries a net positive charge and $AlPO_4$ typically carries a net negative charge at neutral pH. MAA has a higher capacity to bind some antigens than AlOH, potentially due to the net charge of the aluminum adjuvant affecting the ability to bind antigen. In still other exemplary embodiments of the invention described herein, the aluminum adjuvant is Alhydrogel.

One of skill in the art will be able to determine an optimal dosage of aluminum adjuvant that is both safe and effective at increasing the immune response to the targeted dengue 80E antigens of the vaccine composition. For a discussion of the safety profile of aluminum, as well as amounts of aluminum included in FDA-licensed vaccines, see Baylor et al., *Vaccine* 20: S18-S23 (2002). Generally, an effective and safe dose of aluminum adjuvant varies from 200 to 1200 µg/mL concentration. In specific embodiments of the invention, the vaccine comprise between 1.0 and 3.5 mg/mL aluminum adjuvant (up to 1.25 mg elemental aluminum). In alternative embodiments of the formulations and compositions of the present invention, there is about 100, 150, 200, 250, 300, 350, 400, 450 or 500 µg aluminum adjuvant per dose of vaccine.

Formulation with aluminum-based adjuvants comprises an admixture whereby the dengue 80E antigens are allowed to bind to the aluminum adjuvant, e.g. Alhydrogel, such that ≥75% of the antigen is bound to the aluminum hydroxide. The formulation and fill of the DEN1-80E+Alhydrogel vaccine (HBV-001 D1) under cGMP to support clinical development is described in Example 3.

As stated above, one aspect of the present invention provides vaccines and compositions which comprise dengue 80E antigens in combination with an adjuvant. A preferred adjuvant is an ISCOM adjuvant. In the formulations and methods provided herein, the ISCOM adjuvant comprises a saponin, cholesterol, and a phospholipid, and forms an immune-stimulating complex or ISCOM. The potent adjuvant activity of saponins, which are typically isolated from the bark of the *Quillaia saponaria* tree, was first documented over 80 years ago (for review, see Barr and Mitchell, *Immunology and Cell Biology* 74: 8-25 (1996); and Skene and Sutton, *Methods* 40: 53-59 (2006)). Compared to aluminum adjuvants, ISCOM-type adjuvants or ISCOMs are able to provoke a broader immune response to a co-administered antigen, comprising both T-cell and antibody responses. However, a potential for toxicity and haemolytic activity was found, limiting the promise of saponins for human or animal use at that time.

Since then, it was discovered that saponins, when combined with cholesterol and phospholipid, form a characteristic particle having a caged-like structure comprised of twenty or more subunits. This unique structure contributes to the adjuvant activity of the ISCOMs. Additionally, the incorporation of saponins into ISCOMs, together with cholesterol and phospholipid, was shown to eliminate the haemolytic activity of saponins. It was also shown that less adjuvant was needed to induce an immune response when ISCOMs were utilized as adjuvant compared to free saponins (see Skene and Sutton, supra). For these reasons, ISCOMs have been intensely studied as potential vaccine adjuvants.

To this end, the present invention relates to pharmaceutical compositions comprising dengue 80E antigens, an ISCOM adjuvant, and a pharmaceutically acceptable carrier, said ISCOM-adjuvant comprising a saponin, cholesterol, and a phospholipid, wherein said dengue 80E antigens constitute approximately 80% of the length of wild type E starting from amino acid residue 1 at its N-terminus, such that said E protein is secretable into growth medium when expressed recombinantly in a host cell. The compositions described above may further comprise an aluminum salt adjuvant.

In preferred embodiments of this aspect of the invention, the DEN1, DEN2, and DEN3 80E antigens included in the composition are monomeric and the DEN4 80E antigen is dimeric. It has been shown herein (see Example 6) that a tetravalent composition comprising monomeric forms of DEN1, DEN2, and DEN3 80E protein subunits and a dimeric form of DEN4 (DEN4-80EZip) can induce a balanced, tetravalent immune response in rhesus monkeys and can provide protection against viral challenge. The compositions described above may further comprise an aluminum salt adjuvant.

In alternative embodiments of this aspect of the invention, the DEN1-80E, DEN2-80E, DEN3-80E and DEN4-80E proteins in the composition are monomeric. In such embodiments, the DEN4 component is present in an amount that is about 1.5 to about 3 times the individual amounts of DEN1, DEN2, and DEN3 proteins, preferably about 2 times the amount of the DEN1, DEN2, and DEN3 components (proteins).

In exemplary embodiments of this aspect of the invention, the ISCOM adjuvant is the ISCOMATRIX® adjuvant, a saponin-based adjuvant. Formulation with ISCOMATRIX® adjuvant comprises an admixture where the 80E antigens are delivered together with the adjuvant.

In alternative embodiments of the invention, the vaccine compositions are formulated with both an aluminum-based adjuvant and an ISCOM or saponin-based adjuvant.

Dengue Virus Envelope Protein Subunits

It has been shown herein (see Example 6) that a tetravalent composition comprising monomeric forms of DEN1-80E, DEN2-80E, and DEN3-80E protein subunits and a dimeric form of DEN4 (DEN4-80EZip) can induce a balanced, tetravalent immune response in rhesus monkeys and can provide protection against viral challenge. Accordingly, in some preferred embodiments of this aspect of the invention, the DEN1, DEN2, and DEN3 80E antigens included in the composition are monomeric and the DEN4 80E antigen is dimeric. The formation of dengue 80E protein dimers is described, infra.

It has also been shown herein (see Example 7) that high, balanced immune responses against all four dengue types can be achieved by adjusting the antigenic content of the DEN4-80E component so that the amount of the DEN4 antigen component (either DEN4-80E or DEN4-80EZip) is approximately double the amount of DEN1-80E, DEN2-80E, or DEN3-80E antigen present in the composition. Accordingly, the invention provides immunogenic compositions comprising an effective amount of purified dengue virus envelope ("E") proteins of serotype DEN1-80E, DEN2-80E, DEN3-80E, and DEN4-80E, a pharmaceutically acceptable excipient, and an effective amount of adjuvant; wherein the E proteins each constitute approximately 80% of the length of wild type E starting from amino acid residue 1 at its N-terminus, such that said E protein is secretable into growth medium when expressed recombinantly in a host cell; and wherein the composition induces the production of neutralizing antibodies in human subjects; wherein the antigenic content of the DEN4 component is about 1.5 to about 3 times the individual antigenic content of the DEN1, DEN2, or DEN 3 components. In preferred embodiments of this aspect of the invention, the ratio of DEN1:DEN2:DEN3:DEN4 antigens in the compositions is approximately 1:1:1:2.

In some embodiments of this aspect of the invention, the DEN4 component is DEN4-80E. Thus, the composition comprises monomers of DEN1-80E, DEN2-80E, DEN3-80E and DEN4-80E. In alternative embodiments of this aspect of the invention, the DEN4 component is DEN4-80EZip. In such alternative embodiments, the composition comprises monomers of DEN1-80E, DEN2-80E, and DEN3-80E and a dimer of DEN4-80EZip.

In a preferred embodiment of the invention, the recombinant protein component(s) of the dengue virus vaccine formulation (DEN1-80E, DEN2-80E, DEN3-80E, DEN4-80E, and/or DEN4-80EZip) described herein are produced by a eukaryotic cell culture expression system, specifically the *Drosophila melanogaster* S2 cell system (Johansen, H. et al., *Genes Dev*. (1989) 3:882-889; Ivey-Hoyle, M., *Curr. Opin. Biotechnol*. (1991) 2:704-707; Culp, J. S., et al., *Biotechnology* (NY) (1991) 9:173-177). This method of expression successfully produces truncated recombinant envelope proteins from Flaviviruses, such as dengue serotypes 1-4, JE, TBE and WN. These proteins are truncated at the C-terminus, leaving approximately 80% of the native envelope protein (80E). The truncation deletes the membrane anchor of the protein, thus allowing it to be secreted into the extracellular medium, facilitating recovery; the truncation also deletes the stem portion, which has little immunogenic effect. Furthermore, the expressed proteins have been shown to be properly glycosylated and to maintain native conformation as determined by reactivity with a conformationally sensitive monoclonal antibody, 4G2.

As previously described (Ivy et al., U.S. Pat. No. 6,136,561; Ivy et al., U.S. Pat. No. 6,165,477; McDonell et al., U.S. Pat. No. 6,416,763; Ivy et al., U.S. Pat. No. 6,432,411; and Peters et al., U.S. Pat. No. 6,749,857) and, used herein, DEN1-80E, DEN2-80E, DEN3-80E, DEN4-80E, and DEN4-80EZip refer to proteins that span a dengue envelope protein, preferably one starting from the N-terminal amino acid of the envelope protein and ending at an amino acid in the range of the $395^{th}$ to $401^{st}$ amino acid, for example, such 80E can be the protein comprising amino acids 1 to 395 of dengue virus type 2. As described in Peters et al., U.S. Pat. No. 6,749,857, the recombinant 80E protein may optionally contain a dimerization domain linked to the 80E protein by a floppy linker (e.g. DEN4-80EZip). The inclusion of dimeric forms of the proteins is used to modulate the immune response to selected components and results in the induction of balanced tetravalent responses. Expression of DEN-80E proteins is described in Example 1. In preferred embodiments of the invention, a tetravalent composition is provided wherein the DEN4 protein component is dimeric (e.g. DEN4-80EZip).

Dimeric 80E protein subunits, e.g. DEN4 80E dimers, can be produced by means known in the art (See e.g. Peters et al., U.S. Pat. No. 6,749,857 B1). Briefly, three basic approaches are described by Peters et al, supra, to construct dimeric 80% E molecules. The first approach involves using tandem copies of 80% E covalently attached to each other by a flexible linker. The stretch of amino acids covalently linking the two copies of DEN2 80% E is designed to serve as a flexible tether allowing the two 80% E molecules to associate in native head-to-tail dimeric orientation while maintaining their covalent attachment to each other. It would be readily apparent to one of ordinary skill in the art to select other linker sequences as well. The present invention is not limited to the specific disclosed linkers, but, to any amino acid sequence that would enable the two 80% E molecules to associate in native head to tail dimeric orientation while maintaining their covalent attachment to each other.

A second approach involves addition of a carboxy-terminal leucine zipper domain to monomeric 80% E to enhance dimerization between two 80% E-leucine zipper molecules. Two versions of this approach can be adopted. One version includes a disulfide bond linking the leucine zipper domains resulting in a covalently linked dimer product, while the other is based on the non-covalent association of the leucine zipper domains. The leucine zipper domain is designed to dimerize with the identical sequence from another 80% E Zipper molecule. The formation of a non-covalently linked leucine zipper will enhance the dimerization of the 80% E molecules, which may associate in native head to tail conformation by virtue of the flexible linker connecting the 80% E molecules with the leucine zipper domain. The leucine zipper domain is designed to dimerize with the identical sequence from another 80% E Zipper molecule. Once the leucine zipper dimerizes, a disulfide bond forms between the two ends, resulting in a covalently linked dimer product. The formation of a covalently linked leucine zipper will enhance the dimerization of the 80% E molecules, which may associate in native head to tail conformation by virtue of the flexible linker connecting the 80% E molecules with the leucine zipper domain.

The final approach used to enhance dimerization of 80% E is the addition of a helix-turn-helix domain to the carboxy terminal end of 80% E. The helix-turn-helix domain from one modified 80% E molecule will associate with that of another to form a dimeric four-helix bundle domain. The formation of a non-covalently associated four helix bundle domain will enhance the dimerization of the 80% E molecules which may associate in the native head to tail conformation by virtue of the flexible linkers connecting 80% E to the helix bundle.

In another embodiment of the invention, DEN-80E is defined more broadly as a dengue virus envelope protein subunit that comprises six disulfide bridges at Cys1-Cys2, Cys3-Cys8, Cys4-Cys6, Cys5-Cys7, Cys9-Cys10 and Cys11-Cys12; wherein the protein has been secreted as a recombinant protein from *Drosophila* cells; and wherein the protein generates neutralizing antibody responses to the homologous flavivirus when administered to human subjects.

In a more preferred embodiment, the recombinant dengue virus envelope protein subunit further comprises the disulphide pattern described and a hydrophilicity profile characteristic of a homologous 80% portion of an envelope protein (80E) starting from the first amino acid at the N-terminus of the native dengue virus envelope protein. In other words, amino acids can be substituted in the sequence comprising dengue virus 80E so long as the disulphide and hydrophilicity profile is maintained to ensure that the recombinant subunit proteins retain a native-like structure and appropriate immunogenicity (ability to elicit virus neutralizing antibodies).

Preferably, the dengue virus 80E subunit is expressed using a Master Cell Bank in serum free media and purified by chromatography as previously described (Ivy et al., U.S. Pat. No. 6,432,411). Manufacture of a batch of DEN1-80E under cGMP to support clinical testing is described in Example 2.

In contrast to the added benefit described for inclusion of non-structural proteins such as non-structural protein 1 (NS1) in dengue virus formulations tested in animals (McDonell et al., U.S. Pat. No. 6,416,763), the DEN-80E proteins of the invention serve as a potent, immunogenic vaccines in human subjects even without inclusion of NS1.

Administration and Use

The present invention provides a means for preventing or attenuating disease that results from infection by dengue viruses. As used herein, a vaccine is said to prevent or attenuate a disease if administration of the vaccine to an individual results either in the total or partial immunity of the individual to the disease, or in the total or partial attenuation (i.e., suppression) of symptoms or conditions associated with the disease.

Accordingly, the invention relates to a method for raising a protective immune response in a human patient, the method comprising administering a therapeutically effective amount of an immunogenic composition as described anywhere throughout the specification to the patient.

The therapeutic compositions of the described invention can be administered parenterally by subcutaneous, intramuscular, or intradermal injection; however, other systemic modes of administration may also be employed. The preferred method of administration for the present invention is the intramuscular route. Thus, in some embodiments of the methods of the invention, the composition is administered to the patient via the intramuscular route. In alternative embodiments, intradermal or subcutaneous delivery is contemplated.

Also provided herein is a method of providing immune protection in humans against dengue virus induced disease comprising administering an effective amount of the compositions of the invention to the patient, thereby providing protection from dengue disease. In this aspect of the invention, the preferred route of administration is selected from the group consisting of: intramuscular, subcutaneous and intradermal.

The invention also relates to a method for raising a protective immune response in a human patient, the method comprising administering a therapeutically effective amount of an immunogenic composition comprising a purified dengue virus envelope ("E") protein and a pharmaceutically acceptable excipient, wherein the E protein constitutes approximately 80% of the length of wild type E starting from amino acid residue 1 at its N-terminus, such that said E protein is secretable into growth medium when expressed recombinantly in a host cell; and an effective amount of adjuvant, wherein the vaccine induces the production of neutralizing antibodies in human subjects.

Another aspect of the present invention provides an immunogenic composition comprising an effective amount of purified dengue virus envelope ("E") proteins of serotype DEN-1, DEN-2, DEN3, and DEN-4, a pharmaceutically acceptable excipient, and an effective amount of adjuvant; wherein the E proteins each constitute approximately 80% of the length of wild type E starting from amino acid residue 1 at its N-terminus, such that said E protein is secretable into growth medium when expressed recombinantly in a host cell; and wherein the DEN-4 E protein is optionally dimeric; for the prevention or treatment of dengue disease and/or dengue infection. In some aspects of the invention, the compositions described herein are to be administered to immunodeficient populations. In further aspects, the compositions are to be administered to pediatric populations.

In some embodiments of this aspect of the invention the DEN4 component of the composition is DEN4-80EZip. In alternative embodiments, the DEN4 component is DEN4-80E or DEN4-80Ezip and the amount of the DEN4 protein is about 1.5 to about 3 times the amount of the DEN1-80E, DEN2-80E, or DEN3-80E component.

Other aspects of this invention also describe the use of a composition as described above or throughout the specification for the manufacture of a medicament for the treatment or prevention of dengue infection or disease caused thereby.

The active pharmaceutical ingredients of the compositions described herein (dengue 80E and/or dengue 80Ezip) are delivered to the patient in a "therapeutically effective amount," i.e. an amount that is physiologically significant, as described in the Summary of the Invention. The active ingredients of the compositions of the invention are present in a physiologically significant amount if the administration of the composition to a patient results in a detectable change in the physiology of the recipient patient. In the present invention, a detectable change in the recipient patient is the induction of a neutralizing antibody against the homologous dengue virus.

The active vaccine of the invention can be used alone or in combination with other active vaccines such as those containing other active subunits to the extent that they become available. Corresponding or different subunits from one or several viruses or serotypes may be included in a particular formulation. The active vaccine of the invention may further comprise a pharmaceutically acceptable excipient.

Many different techniques exist for the timing of the immunizations when a multiple administration regimen is utilized. It is preferable to use the compositions of the invention more than once to increase the levels and diversities of expression of the immunoglobulin repertoire expressed by the immunized subject. Typically, if multiple immunizations are given, they will be given one to two months apart. The preferred immunization schedule of the invention is to immunize the subjects a 0, 1, and 2 months. Other immunizations schedules can also be utilized. For example, alternative immunization schedules such as 0, 1 and 3 months, or 0, 1 and 6 months could be used.

To immunize subjects against dengue virus-induced disease for example, the vaccines containing the subunits are administered to the subject in conventional immunization protocols involving, usually, multiple administrations of the vaccine. Administration is typically by injection, typically intramuscular or subcutaneous injection; however, other systemic modes of administration may also be employed.

Immunogenic Compositions

As stated, supra, one aspect of the present invention is an immunogenic composition comprising an effective amount of purified dengue virus envelope ("E") proteins of serotype DEN-1, DEN-2, DEN3, and DEN-4, a pharmaceutically acceptable excipient, and an effective amount of adjuvant; wherein the E proteins each constitute about 80% of the length of wild type E starting from amino acid residue 1 at its N-terminus; wherein the DEN-4 E protein is dimeric; and wherein the composition induces the production of neutralizing antibodies in human subjects.

In embodiments of this aspect of the invention, the amount of Dengue E protein for each serotype is from about 1 μg to about 150 μg, from about 1 μg to about 10 μg, from about 1 μg to about 5 μg, from about 2 μg to about 4 μg, from about 3 μg to about 6 μg, from about 5 μg to about 25 μg, from about 10 μg to about 20 μg, from about 5 μg to about 10 μg, from about 20 μg to about 25 μg, from about 40 μg to about 60 μg, from about 75 μg to about 125 μg, or from about 90 μg to about 110 μg. In alternative embodiments, the amount of each dengue protein is about 1 μg, about 2 μg, about 3 μg, about 4 μg, about 5 μg, about 6 μg, about 7 μg, about 8 μg, about 9 μg, about 10 μg, about 15 μg, about 20 μg, about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 110 μg, about 120 μg, about 130 μg, about 140 μg, or about 150 μg. In preferred embodiments of the invention, the amount of each dengue E protein is approximately 3 μg, approximately 6 μg, approximately 10 μg, approximately 20 μg, approximately 50 μg, approximately 100 μg, 3 μg, 6 μg, 10 μg, 20 μg, 50 μg, or 100 μg.

Also provided is an immunogenic composition comprising an effective amount of purified dengue virus envelope ("E") proteins of serotype DEN-1, DEN-2, DEN3, and DEN-4, a pharmaceutically acceptable excipient, and an effective amount of adjuvant; wherein the E proteins each constitute about 80% of the length of wild type E starting from amino acid residue 1 at its N-terminus; wherein the amount of DEN4 protein is about 1.5 to about 3 times the individual amounts of DEN1, DEN2, and DEN3 proteins, and wherein the composition induces the production of neutralizing antibodies in human subjects. In this aspect of the invention, the DEN1, DEN2, DEN3 and DEN4 E proteins are monomeric (e.g. DEN-80E) or the DEN1, DEN2, and DEN3 E proteins are monomeric and the DEN4 protein is dimeric.

In this aspect of the invention, the dengue E proteins in the composition are present in the amounts described above, with the proviso that the DEN4 E protein, whether monomeric or dimeric, is present in an amount that is about 1.5 to about 3 times the individual amounts of the DEN1, DEN2, and DEN3 E proteins. Thus, merely as an example, if the DEN1, DEN2, and DEN3 E proteins are present in the composition in an amount of about 3 μg, then the DEN4 E protein is present in the composition in an amount of about 4.5 μg to about 9 μg, preferably about 6 μg. As a further example, if the DEN1, DEN2, and DEN3 E proteins are present in the composition in an amount of about 10 μg, then the DEN4 E protein is present in the composition in an amount of about 15 μg to about 30 μg, preferably about 20 μg. In another further example, if the DEN1, DEN2, and DEN3 E proteins are present in the composition in an amount of about 50 μg, then the DEN4 E protein is present in the composition in an amount of about 75 μg to about 150 μg, preferably about 100 μg. One skilled in the art will realize that while the amount of the DEN1, DEN2, and DEN3 E proteins are approximately equal, the amounts can vary and do not have to be present in an exact 1:1:1 ratio. One skilled in the art will be able to determine an optimal dose of each DEN E protein that is both safe and induces a balanced, tetravalent immune response against DEN1, DEN2, DEN3 and DEN4

In preferred embodiments of the invention, the immunogenic composition comprises about 3 μg DEN1, DEN2, and DEN3 E proteins and about 6 μg of DEN4 E protein (DEN4-80E or DEN4-80EZip). In a further preferred embodiment, the immunogenic composition comprises about 10 μg DEN1, DEN2, and DEN3 E proteins and about 20 μg of DEN4 E protein (DEN4-80E or DEN4-80EZip). In a further preferred embodiment, the immunogenic composition comprises about 50 µg DEN1, DEN2, and DEN3 E proteins and about 100 µg of DEN4 E protein (DEN4-80E or DEN4-80EZip).

Pharmaceutically acceptable carriers useful in the compositions of the invention include any compatible agent that is nontoxic to patients at the dosages and concentrations employed, such as water, saline, dextrose, glycerol, ethanol, buffers, and the like, and combinations thereof. The carrier may also contain additional components such as a stabilizer, a solubilizer, a tonicity modifier, such as NaCl, $MgCl_2$, or $CaCl_2$ etc., a surfactant, and mixtures thereof.

According to the described invention, an "effective amount" of a therapeutic composition is one which is sufficient to achieve a desired biological effect. Generally, the dosage needed to provide an effective amount of the composition will vary depending upon such factors as the subject's age, condition, sex, and extent of disease, if any, and other variables which can be adjusted by one of ordinary skill in the art. The antigenic preparations of the invention can be administered by either single or multiple dosages of an effective amount. Effective amounts of the compositions of the invention can vary from 0.01-500 μg per product per dose, more preferably from 1-100 μg per product per dose, and most preferably 5-50 μg per product per dose. The compositions of the invention may further comprise a pharmaceutically acceptable excipient.

In accordance with the present invention, the production of DEN1-80E, DEN2-80E, DEN3-80E, and DEN4-80EZip active ingredients and HBV-001 D1 and tetravalent dengue vaccines at large scale and under cGMP to support administration to human subjects is shown (Examples 1-4). Determination of the safety and immunogenicity (efficacy) of vaccines of the invention in non-human primates and healthy adult volunteers (Examples 5-8) is described. Embodiments of the dengue vaccines of the invention combine two important aspects. In one aspect, the inherent safety of recombinant subunit proteins combined with adjuvants provide the optimal approach for prevention of a disease in healthy and immunocompromised individuals. In a second aspect the production of conformationally relevant recombinant DEN1-80E, DEN2-80E, DEN3-80E, DEN4-80E and DEN4-80EZip, antigens under current good manufacturing practices (cGMP), in quantities sufficient to be of practical use, results in vaccines which induce balanced tetravalent virus neutralizing antibodies in non human primates and human subjects, providing a mechanism for protection against disease. The unique combination of the monomeric and dimeric 80E proteins and in various ratios is utilized to assure tetravalent balance which is critical for minimizing the risk of exacerbated disease such as DHF. The combination of these novel aspects results in the novel invention of dengue virus vaccines which are safe and effective in human subjects. These vaccine formulations are further characterized by the unexpected finding that inclusion of the non-structural protein NS1 is not required for effective immunogenicity and protection. Moreover, the disclosed dengue vaccines address the technical problem of inducing relevant protective immune responses in vaccinated individuals while maintaining an acceptable safety profile, in particular for those subjects at highest risk of severe disease, including infants, the elderly, and immunocompromised.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

Example 1

Expression and Purification of Dengue 80E Proteins in the *Drosophila* S2 System The expression plasmid pMttbns (derived from pMttPA) contains the following elements: *Drosophila melanogaster* metallothionein promoter, the human tissue plasminogen activator secretion leader (tPAL) and the SV40 early polyadenylation signal. A 14 base pair BamHI (restriction enzyme from *Bacillus amyloliqufacience*) fragment was excised from the pMttbns vector to yield pMttΔXho that contains a unique XhoI (restriction enzyme from *Xanthomonas holicicola*) site in addition to an existing unique BglII (restriction enzyme from *Bacillus globigii*) site. This expression vector promotes the secretion of expressed proteins into the culture medium. Dengue sequences were introduced into the pMttΔXho vector using these unique BglII and XhoI sites. Dengue sequences used for studies described herein are represented by SEQ ID NO's 1-5, as follows: (1) SEQ ID NO:1; DEN1 prM-80E; (2) SEQ ID NO:2; DEN2 prM-80E; (3) SEQ ID NO:3; DEN3 prM-80E; (4) SEQ ID NO:4; DEN4 prM-80E; and (5) SEQ ID NO:5; DEN4 prM-80EZip. For the expression of carboxy-truncated dengue envelope proteins, the relevant gene fragment was amplified from viral RNA or cDNA clones. The synthetic prM80E (pre-membrane protein-80% glycoprotein E) gene fragment included two stop codons immediately following the last dengue codon.

S2 cells were co-transformed with both the expression plasmid and the pCoHygro selection plasmid that encodes hygromycin resistance utilizing the (i) calcium phosphate co-precipitation method or (ii) Cellfectin (Invitrogen Kits, Carlsbad, Calif.) according to the manufacturer's recommendations. Cells were co-transformed with 20 μg total DNA with a 20:1 ratio of expression plasmid to selection plasmid. Transformants were selected with hygromycin B (Roche Molecular Biochemicals, Indianapolis, Ind.) at 300 μg/ml. Following selection, cells were adapted to growth in the serum free medium, Excel 420 (JRH, Lenexa, Kans.). For expression studies, cells were grown in Excel 420, 300 μg/ml hygromycin, and induced with 200 μM CuSO4. Cells were seeded at a density of $2\times10^6$ cells/ml and allowed to grow for 6-7 days. Under optimal conditions, cell densities of 1.5 to $2\times10^7$ cells/ml were achieved after 6-7 days of growth. The culture supernatant was examined for expressed protein by SDS-PAGE and Western blot.

For the detection of the DEN-80E on Western blots, rabbit polyclonal anti-dengue virus antibody developed against purified inactivated dengue virus followed by an anti-rabbit IgG-alkaline phosphatase conjugated secondary antibody was used. The blots were developed with NBT/BCIP (Sigma Chem. Co., St. Louis, Mo.) solid phase alkaline phosphatase substrate.

Purification of the DEN1-80E, DEN2-80E, DEN3-80E, DEN4-80E or DEN4-80EZip, protein was accomplished by immunoaffinity chromatography (IAC) using the monoclonal antibody (MAb) 4G2. Briefly, the procedure involves the clarification of the post-expression medium. The crude material is then loaded onto the IAC column, which contains immobilized MAb that is covalently coupled via N-hydroxysuccinimide chemistry. After the sample is loaded, the matrix is washed with 10 mM phosphate buffered saline (PBS), pH 7.2, containing 0.05% (v/v) tween-20 (PBST, 140 mM NaCl). Bound protein is eluted from the IAC column with 20 mM glycine buffer, pH 2.5. The eluate is neutralized then buffer exchanged against PBS. The purification products are routinely analyzed by SDS-PAGE with Coomassie or silver staining, Western blot, UV absorption, and enzyme linked immunosorbent assay (ELISA) to determine purity, identity, quantity, and bioactivity, respectively. In addition, samples were analyzed by N-terminal amino acid sequencing and amino acid analysis. These analyses provided confirmation of identity and quantity of the purification products.

Figure 1B:
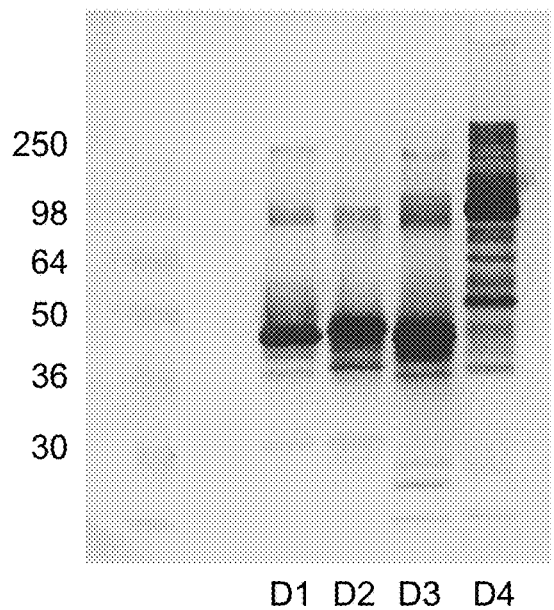

FIGS. 1A-B provide representative SDS-PAGE (1A) and Western blot (1B) profiles of the purified DEN-80E proteins. For the analysis, samples were run under non-reducing conditions. The DEN1-80E, DEN2-80E, and DEN3-80E molecules migrate as a single band with a relative molecular weight consistent with that determined from the amino acid composition (i.e., 45 kD). The DEN4-80EZip protein migrates primarily as a dimer under non-reducing conditions with an apparent molecular weight of approximately 90 kD.

Example 2

Production of cGMP Lots of DEN1-80E, DEN2-80E, DEN3-80E, or DEN4-80EZip

A Master Cell Bank (MCB) was prepared from each of the S2 cell lines under cGMP conditions. The cGMP manufacturing process involves expansion of the S2 MCB cell line to a stirred tank bioreactor and then harvesting the culture medium containing the secreted protein. The cells are separated from the culture medium by filtration utilizing depth filters. The DEN1-80E, DEN2-80E, DEN3-80E, or DEN4-80EZip was then purified from the resultant clarified supernatant by immunoaffinity chromatography using the 4G2 monoclonal antibody. The immunoaffinity purification product was subsequently taken through a low pH viral inactivation step and a viral filtration step using membranes with pore sizes capable of removing 20 nm particles. The ability to take the recombinant subunit vaccine components through low pH viral inactivation and viral filtration steps is an advantage over live attenuated vaccines where this is not possible. These viral clearance steps significantly simplify adventitious agent testing and provide an additional level of safety for the product. The final processing of the DEN-80E proteins involved buffer-exchange and concentration by ultrafiltration followed by a final filtration through a 0.2 μm filter.

The manufacture of lots of DEN1-80E, DEN2-80E, DEN3-80E, or DEN4-80EZip under cGMP was accomplished as described below. Vials of each MCB were thawed and the contents of each thawed vial was cultured in a 10 mL volume of EX-CELL medium for 5 days at 26° C. Each culture was expanded to 500 mL disposable shake flasks. The cultures were grown until a cell density of $1.5 \times 10^7$/mL was achieved. Flasks were pooled and used to inoculate a larger culture in a disposable shake flask which was then grown for 3 to 4 days. The culture was grown until a density of $2 \times 10^7$ cells/mL was achieved. The culture was then expanded to multiple cultures in disposable shake flasks. These cultures were grown until an average cell density of $1.6 \times 10^7$ cells/mL was achieved. The cells from the flasks were pooled and used to inoculate a 20 L stainless steel bioreactor. The culture was grown until a cell density of $1.2 \times 10^7$ cells/mL was achieved. The appropriate amount of cells from the 20 L bioreactor were transferred to a 100 L stainless steel bioreactor to achieve an initial cell density of $2 \times 10^6$ cells/mL. The culture was grown until a cell density of $>4.0 \times 10^6$ cells/mL was achieved. The culture was then induced by adding copper sulfate to the culture to achieve a final concentration of 0.2 mM. The culture was then grown for 5 days. The 100 L of each culture was harvested by depth filtration using a 0.45 μm filter cartridge which was followed by a 0.2 μm filter cartridge. The filtrate was collected in 10 L volumes in single use bags and stored at −20° C.

The DEN1-80E, DEN2-80E, DEN3-80E, or DEN4-80EZip bulk harvest was thawed at ambient temperature (15-25° C.) for approximately 24 hours. Particulates were then removed by passage of the material through a 5 μm pore size filter. The filtered bulk harvest was loaded directly onto a 4G2-sepharose column. After loading, the column was washed with 11 mM PBS, pH 7.1, containing 0.05% Tween-20 (PBST) then retained 80E was eluted by lowering the pH with a glycine buffer. Sub-batches were pooled then viral inactivated by lowering the pH to a final pH of 3.8 and incubating the material at ambient temperature (15-25° C.) for 16-24 hours after which the pH was adjusted to 7.0±0.5. The material was passed through a 0.2 μm pre-filter to remove small particulates then viral filtered using a 20 nm pore sized membrane. The material was then concentrated and buffered exchanged by ultrafiltration and a final sterile filtration was accomplished by passage through a 0.2 μm filter directly into sterile bags. The purified 80E biologic substances underwent extensive safety, identity, strength, and purity assessments prior to release for formulation into the vaccine products.

Example 3

Formulation of the HBV-001 D1 Vaccine for Use in Clinical Studies

Formulation of the monovalent DEN1-80E alum adsorbed (HBV-001 D1) vaccine was conducted under cGMP. Briefly, the purified biologic substance DEN1-80E described in Example 2 was thawed and transferred into a Class 100 laminar flow area. The DEN1-80E was diluted with sterile Dulbecco's Phosphate Buffered Saline (DPBS) to achieve a final protein target concentration of 0.20 mg/mL and the diluted 80E solution was sterile filtered. DPBS and Alhydrogel '85' were volumetrically added the diluted DEN1-80E solution to a final Aluminum concentration of 2.50 mg/mL. The solution was mixed gently overnight at 2-8° C.

Following the overnight adsorption the quantity of DEN1-80E protein which was not adsorbed was determined. A minimum of 75% adsorption was required to move forward to fill of the HBV-001 D1 vaccine. The appropriate quantities of the HBV-001 D1 vaccine was transferred into prepared sterile vials. The filled vials were stoppered, sealed, and crimped. The filled vials of vaccine were stored at 2 to 8° C. Extensive safety, strength, identity, potency, and purity testing was conducted prior to use of the vaccine in clinical studies.

Example 4

Formulation of the Tetravalent Dengue Antigen for Use in Clinical Studies

Formulation of the tetravalent DEN-80E vaccine was conducted under cGMP. Briefly, the purified biologic substances DEN1-80E, DEN2-80E, DEN3-80E, and DEN4-80EZip described in Example 2 were thawed and transferred into a Class 100 laminar flow area. The thawed antigens were sterile filtered and the protein concentration post-filtration determined. The DEN-80E antigens were each independently diluted with sterile Dulbecco's Phosphate Buffered Saline (DPBS) to achieve a final protein target concentration of 0.50 mg/mL. The four protein solutions were then mixed volumetrically at a ratio of 1:1:1:2 for DEN1-80E:DEN2-80E:DEN3-80E:DEN4-80EZip to produce a tetravalent solution containing DEN1-80E at 0.1 mg/mL, DEN2-80E at 0.1 mg/mL, DEN3-80E at 0.1 mg/mL, and DEN4-80EZip at 0.2 mg/mL. The appropriate quantities of the tetravalent vaccine mixture was transferred into prepared sterile vials. The filled vials were stoppered, sealed, and crimped. The filled vials of vaccine were stored at 2 to 8° C. Similar formulations containing DEN1-80E, DEN2-80E, DEN3-80E and DEN4-80E were also prepared to support clinical testing. Extensive safety, strength, identity, potency, and purity testing was conducted prior to use of the vaccine in clinical studies. The tetravalent antigen is administered alone or mixed in accordance with Good Clinical Practices with sterile, filled adjuvant prior to administration to human subjects.

Example 5

Clinical Testing of the HBV-001D1 Dengue Type 1 Recombinant Subunit Vaccine

The HBV-001 D1 vaccine manufactured under cGMP as described in Example 3 was tested in a clinical trial. The single-center, double-blind, randomized, Phase 1 study to evaluate the HBV-001 D1 biologic product in healthy adult volunteers evaluated two different dose levels of the vaccine's active ingredient (DEN1-80E) with the same amount of Alhydrogel '85' adjuvant. Subjects received a single IM injection of study vaccine at Weeks 0, 4 and 8. The design of the study is summarized in Table 1 below.

TABLE 1

Design of the Clinical Study HBV-001-C-101

| Treatment | Cohort |
|---|---|
| Low Dose DEN1-80E (10 μg) + Alhydrogel (1.25 mg of elemental Al) | Cohort 1 (N = 6 active, 2 placebo) |
| High Dose DEN1-80E (50 μg) + Alhydrogel (1.25 mg of elemental Al) | Cohort 2 (N = 6 active, 2 placebo) |

Safety and tolerability were assessed throughout the study by targeted physical examination, routine laboratory testing (hematology, clinical chemistry and urinalysis) and the recording of vital signs and adverse events in study volunteers. In addition, subjects used diary cards for 14+/−2 days after each vaccination to record reactogenicity and tolerance data as well as specific adverse events. Efficacy assessments in this study included the determination of the rate and extent of virus neutralizing antibody titers (i.e., immunogenicity), as determined by $PRNT_{50}$ (plaque reduction neutralization test) assay of ≥1:10. There were no safety signals identified in the study suggesting that the vaccine is safe for human subjects.

Immunogenicity data from the immunized individuals are summarized in Table 2. Of the 6 vaccine recipients in the low-dose cohort, all subjects were negative for neutralizing antibody titers at Weeks 0, 2, and 4. The majority of subjects (4/6) had developed neutralizing antibodies by Week 10, which was 2 weeks after the third vaccine dose. No subject displayed detectable antibodies by Week 34. One subject (007) showed a positive result beginning at Week 6 (2 weeks after the second vaccine dose) which was also present at Week 10 but undetectable at Week 34 (26 weeks post Dose 3).

Of the 6 vaccine recipients in the high-dose cohort, all subjects were negative for neutralizing antibody titers at Weeks 0, 2, and 4. One subject showed positive results beginning at Week 6 (2 weeks after the second vaccine dose). Two subjects displayed neutralizing antibodies at Week 8 (day of third vaccine dose), and the majority of subjects (5/6)) had developed neutralizing antibodies by Week 10. Two subjects continued to display detectable antibody titers at Week 34. This represents the first demonstration of induction of virus neutralizing antibodies for a non-replicating vaccine for dengue in human subjects. All 4 placebo recipients had undetectable antibody titers at all measured time points.

TABLE 2

Summary of Neutralizing Antibody Titers by Subject

| | Subject ID | Visit 1 Week 0 (Dose 1) | Visit 2 Week 2 | Visit 3 Week 4 (Dose 2) | Visit 4 Week 6 | Visit 5 Week 8 (Dose 3) | Visit 6 Week 10 | Visit 7 Week 34 |
|---|---|---|---|---|---|---|---|---|
| Low Dose | 007 | <10 | <10 | <10 | 62 | 19 | 44 | <10 |
| | 013 | <10 | <10 | <10 | <10 | <10 | 30 | <10 |
| | 014* | <10 | <10 | <10 | <10 | <10 | <10 | <10 |
| | 019 | <10 | <10 | <10 | <10 | <10 | 91 | <10 |
| | 020 | <10 | <10 | <10 | <10 | <10 | 32 | <10 |
| | 022 | <10 | <10 | <10 | <10 | <10 | <10 | <10 |
| High Dose | 025 | <10 | <10 | <10 | 182 | 113 | 502 | 18 |
| | 027 | <10 | <10 | <10 | <10 | <10 | 58 | <10 |
| | 028 | <10 | <10 | <10 | <10 | <10 | <10 | <10 |
| | 031 | <10 | <10 | <10 | <10 | <10 | 37 | <10 |
| | 033 | <10 | <10 | <10 | <10 | 12 | 62 | 27 |
| | 041 | <10 | <10 | <10 | <10 | <10 | 14 | <10 |
| Placebo | 011 | <10 | <10 | <10 | <10 | <10 | <10 | <10 |
| | 018 | <10 | <10 | <10 | <10 | <10 | <10 | <10 |

TABLE 2-continued Summary of Neutralizing Antibody Titers by Subject

| Subject ID | Visit 1 Week 0 (Dose 1) | Visit 2 Week 2 | Visit 3 Week 4 (Dose 2) | Visit 4 Week 6 | Visit 5 Week 8 (Dose 3) | Visit 6 Week 10 | Visit 7 Week 34 |
|---|---|---|---|---|---|---|---|
| 036 | <10 | <10 | <10 | <10 | <10 | <10 | <10 |
| 037 | <10 | <10 | <10 | <10 | <10 | <10 | <10 |

Antibody levels were determined by PRNT assay with a minimum detectable titer of 10. Subjects with non-detectable antibody titers are designated with "<10".
*Subject 014 received only one dose of vaccine but completed all study visits and safety assessments The results demonstrate that the HBV-001 D1 vaccine is both safe and capable of inducing an immune response against DEN1 in human patients. Furthermore, this relevant protective immune response was induced in vaccinated individuals without the inclusion of NS1 in the formulation, despite the anticipated requirement for NS1 for potent protection (McDonell et al., U.S. Pat. No. 6,416,763).

Example 6

Testing of the Tetravalent Dengue 80E Recombinant Subunit Vaccine (w/DEN4-80EZip) in Rhesus Macaques A tetravalent formulation comprising the unique combination of the monomeric DEN1-80E, monomeric DEN2-80E, monomeric DEN3-80E, and dimeric DEN4-80EZip was prepared as an admixture with ISCOMATRIX® adjuvant to deliver a dose of 1 µg of each DEN-80E and 47 ISCO units of ISCOMATRIX® adjuvant to Rhesus macaques (Group 1). A second admixture was prepared which comprised the same tetravalent composition but also included a dose of 0.1 µg of NS1 protein from DEN2 (Group 2). Groups of 12 monkeys each were administered 3 doses of either admixture or ISCOMATRIX® alone (Group 3) at 2 month intervals Immunogenicity was assessed 30 days following the third dose of vaccine (study day 150). Antibody titers from individual animals immunized with the tetravalent formulation without NS1 are presented in Table 3. As can be clearly seen, the unique combination of the monomeric and dimeric antigens results in high titer, balanced tetravalent virus neutralizing responses in the animals.

TABLE 3

Virus Neutralizing Antibody Responses Following 3 Doses of Tetravalent Vaccine

| Animal ID | Anti-DEN1 virus response* | Anti-DEN2 virus response* | Anti-DEN3 virus response* | Anti-DEN4 virus response* |
|---|---|---|---|---|
| CT343 | 480 | 622 | 328 | 99 |
| CR14 | 519 | 2979 | 1509 | 447 |
| CN96 | 1365 | 1101 | 959 | 449 |
| CN94 | 277 | 1710 | 744 | 305 |
| CM80 | 1522 | 1897 | 603 | 312 |
| CM50 | 184 | 157 | 166 | 131 |
| CL84 | 151 | 839 | 589 | 781 |
| CL47 | 829 | 584 | 608 | 442 |
| CL25 | NT | 1187 | 302 | 309 |
| CI27 | 725 | 1290 | 1034 | 289 |
| CH97 | 2718 | 767 | 555 | 117 |
| CN32 | 1927 | 867 | 588 | 256 |

Virus neutralizing antibody titers as determined in plaque reduction neutralization tests with a cutoff of 50% reduction Five months after receiving the last dose of vaccine, the animals were challenged with wild type dengue viruses. For the challenge, each group of 12 monkeys each was randomly subdivided into 4 groups of 3 monkeys each for challenge with one of the four dengue viruses. Each monkey was challenged with approximately $10^5$ plaque forming units of the wild type dengue viruses administered by the subcutaneous route. The animals had blood samples taken daily for the next 11 days. The blood samples were assessed for the presence of virus (viremia) by direct plating on Vero cells or amplification on mosquito C6/36 cells and then plating on Vero cells. While Rhesus macaques do not develop disease symptoms when infected with wild type dengue virus, they do develop viremia and prevention of viremia is considered a surrogate for protective efficacy. The challenge data are presented in FIG. 2. While 11/12 control animals who had received ISCOMATRIX® adjuvant only developed viremia following challenge, all animals that received the tetravalent vaccine formulation without NS1 (Group 1) were completely protected from detectable viremia. 11/12 animals receiving the tetravalent vaccine formulation which did contain NS1 (Group 2) were also protected from viremia, but surprisingly one monkey receiving the NS1 containing formulation did develop a single day of viremia. Thus, a tetravalent vaccine formulation containing the unique combination of monomeric and dimeric proteins without NS1 showed balanced tetravalent immunity and complete protection from viral challenge and surprisingly appeared to have shown superior protection compared to a formulation which did contain NS1.

Example 7

Testing of the Tetravalent Dengue 80E Recombinant Subunit Vaccine in Rhesus Macaques The objective of this non-GLP Rhesus monkey study was to: 1) compare the immunogenicity and protective efficacy of the DEN4-80E and DEN4-80EZip and 2) to evaluate the immunogenicity and protective efficacy of DEN4-80E in a tetravalent formulation with the other monomeric DEN-80E recombinant subunits (DEN1-80E, DEN2-80E and DEN3-80E). DEN4-80E and DEN4-80Ezip were evaluated at low, medium and high doses (6, 20 and 100 µg/dose). Likewise the tetravalent formulations were evaluated at low (3, 3, 3, 6 µg of DEN1-80E, DEN2-80E, DEN3-80E and DEN4-80E respectively) medium (10, 10, 10, 20 µg) and high (50, 50, 50, 100 µg) doses. The majority of tested formulations contained ISCOMATRIX® adjuvant at 90 ISCO Units per dose. A negative control group was included that received ISCOMATRIX® adjuvant only, at 90 ISCO Units per dose. For comparative purposes two additional groups were included in the study. A group was included that received the medium dose of DEN4-80E (20 µg) formulated with 225 µg of Alhydrogel and a group that received the medium tetravalent vaccine dose formulated with 37.6 ISCO Units. Each vaccine or control formulation was administered to healthy adult, Rhesus macaques of either sex, weighing more than 3 kg, and which were flavivirus (DEN 1, 2, 3 and 4, and WN) antibody negative by ELISA assay. Three monkeys per group were used when evaluating monovalent DEN4 vaccines and 12 monkeys per group were used to evaluate the tetravalent formulations or the ISCOMA-TRIX® negative control group.

The candidate vaccine formulations described above were administered in 0.5 mL total volume by intramuscular inoculation. Three doses of vaccine were administered at 4 week intervals. Virus neutralizing activity is being determined every four weeks (T=0, 4, 8, 12, 16, 20, 24, 28, 32) using the LiCor based microneutralization assay. LiCor Results for Week 12 (4 weeks post dose 3) are summarized below in Table 4. One of the key conclusions from the week 12 results in that the immunogenicity of DEN4-80E and DEN4-80Ezip are very comparable across the doses evaluated. The geometric mean neutralization titers for DEN4-80E at the low, medium and high doses were 508, 508 and 320 respectively while the titers for DEN4-80Ezip were 640, 1016 and 320. It was also observed that the group receiving the medium DEN4-80E dose adjuvanted with ISCOMATRIX® had a substantially higher geometric mean neutralization titer (508) than the group that received Alhydrogel (32). It was also seen that high balanced responses across all dengue types were achieved in the groups that received the tetravalent vaccine formulations. No clear dose response was observed for either the single component vaccines (DEN4-80E or DEN480E-zip) or the tetravalent vaccine.

TABLE 4

Dengue Serotype Neutralizing Antibody Titers ($LiCor_{50}$ GMT) Induced in Rhesus Macaques at Week 12 (4 weeks post dose 3) by various Recombinant Subunit and Control Formulations

| Group | Monkeys Per Group | Formulation | Anti-DENV-1 $LiCor_{50}$ Titers (GMT) | Anti-DENV-2 $LiCor_{50}$ Titers (GMT) | Anti-DENV-3 $LiCor_{50}$ Titers (GMT) | Anti-DENV-4 $LiCor_{50}$ Titers (GMT) |
|---|---|---|---|---|---|---|
| 1 | 12 | 90 ISCO units ISCOMATRIX ® | 5 | 5 | 5 | 5 |
| 2 | 3 | 100 μg DEN4-80E 90 ISCO units ISCOMATRIX ® | 25 | 20 | 16 | 320 |
| 3 | 3 | 20 μg DEN4-80E 90 ISCO units ISCOMATRIX ® | 32 | 16 | 25 | 508 |
| 4 | 3 | 6 μg DEN4-80E 90 ISCO units ISCOMATRIX ® | 16 | 13 | 20 | 508 |
| 5 | 3 | 100 μg DEN4-80Ezip 90 ISCO units ISCOMATRIX ® | 63 | 32 | 25 | 320 |
| 6 | 3 | 20 μg DEN4-80Ezip 90 ISCO units ISCOMATRIX ® | 63 | 25 | 32 | 1016 |
| 7 | 3 | 6 μg DEN4-80Ezip 90 ISCO units ISCOMATRIX ® | 63 | 32 | 25 | 640 |
| 8 | 3 | 20 μg DEN4-80Ezip 225 μg Alhydrogel | 6 | 5 | 5 | 32 |
| 9 | 12 | 50 μg DEN1-80E 50 μg DEN2-80E 50 μg DEN3-80E 100 μg DEN4-80E 90 ISCO units ISCOMATRIX ® | 381 | 302 | 507 | 180 |
| 10 | 12 | 10 μg DEN1-80E 10 μg DEN2-80E 10 μg DEN3-80E 20 μg DEN4-80E 90 ISCO units ISCOMATRIX ® | 254 | 381 | 508 | 214 |
| 11 | 12 | 3 μg DEN1-80E 3 μg DEN2-80E 3 μg DEN3-80E 6 μg DEN4-80E 90 ISCO units ISCOMATRIX ® | 339 | 285 | 604 | 285 |
| 12 | 12 | 10 μg DEN1-80E 10 μg DEN2-80E 10 μg DEN3-80E 20 μg DEN4-80E 37.6 ISCO units ISCOMATRIX ® | 226 | 214 | 359 | 143 |

NT—not tested;

* $LiCor_{50}$ result of <10 considered 5 for purposes of calculating GM

Example 8

Clinical Testing of the Tetravalent Dengue 80E Recombinant Subunit Vaccine

The tetravalent dengue 80E vaccine manufactured under cGMP is prepared for testing in a clinical trial. The study will consist of a Phase I study of the tetravalent dengue 80E vaccine. The study will be a randomized, double-blind, placebo-controlled, dose escalation study, which will evaluate the safety, tolerability, and immunogenicity of different formulations of a tetravalent (DEN1-80E, DEN2-80E, DEN3-80E, and DEN4-80E) dengue vaccine in healthy flavivirus-naive adults 18 to 45 years of age Immunogenicity data will be collected 1 month after each vaccination, as well as 6 months and 1 year after the third vaccination.

In all, 90 subjects will be enrolled into the study to receive 3 intramuscular injections, of either active vaccine or placebo, administered at 0, 4, and 8 weeks. As shown in Table 5, 3 dose levels of Dengue 1, Dengue 2, Dengue 3, and Dengue 4-80E antigens will be assessed: low dose (3, 3, 3, and 6 μg, respectively), medium dose (10, 10, 10, and 20 μg, respectively), and high dose (50, 50, 50, and 100 μg, respectively) formulations. Within each dose level, specific vaccines tested will include ISCOMATRIX® adjuvanted (with 30 or 60 ISCO units), Alhydrogel™-adjuvanted, or non-adjuvanted formulations.

Brunger, A. et al., (1998) *Acta Crystallogr. D. Biol. Crystallogr.* 54:905-21
Cane, P. A. et al., (1988) *J. Gen. Virol.* 69:1241-46
Bungener et al., (2005) *Vaccine* 23:1232-41
Cardosa, M. J. (1998) *British Med. Bull.* 54:395-405
Cerquetti, M. C. et al., (1983) *Infect. Immun.* 41:1017
Chambers, T. J. et al., (1990) *Annual Rev. Microbiol.* 44:649-88
Chang et al., (2001) *Ann. N.Y. Acad. Sci.* 951:272-85
Chen, W. et al., (1995) *J. Virol.* 69:5186-90
Chowers et al., (2001) *Emerg. Inf. Dis.* 7:675-78
Chu, R. S. et al., (1997) *J. Exp. Med.* 186:1623
Clements et al., (2010) *Vaccine* 28:2705
Comment (2004) *Ann. Inter. Med.* 141:153
Cox, J. C. and Coulter, A. R. (1997) *Vaccine* 15:248-56
Crill, W. and Roehrig J. (2001) *J. Virol.* 75:7769-73
Culp, J. S. et al., (1991) *Biotechnology* 9:173-7
Cuzzubbo et al., (2001) *Clin. Diagn. Lab. Immunol.* 8:1150-55
Dejnirattisai et al., (2010) *Science* 328:745-748
Dharakul, T. et al., (1994) *J. Infect. Dis.* 170:27-33
Eckels, K. H. et al., (1984) *Am. J. Trop. Med. Hyg.* 33:684-89
Edelman, R. et al., (1994) *J. Infect. Dis.* 170:1448-55
Elias et al., (2003) *J. Immunol.* 171:3697-3704
Ennis, F. et al., (1999) *Virology* 259:256-61

TABLE 5

Investigational Formulations to be Assessed in Protocol 001

| Antigen Dose (μg) by Dengue Type (DEN1, DEN2, DEN3, DEN4) | Non-adjuvanted | ISCOMATRIX ® (30 ISCO units) | ISCOMATRIX ® (60 ISCO units) | Alhydrogel (225 μg aluminum) | Placebo | Sample Size (N = 90) |
|---|---|---|---|---|---|---|
| 3, 3, 3, 6 (low dose) | NA | 8 | 8 | NA | 6 | 22 |
| 10, 10, 10, 20 (medium dose) | 8 | 8 | 8 | 8 | 6 | 38 |
| 50, 50, 50, 100 (high dose) | 8 | 8 | 8 | NA | 6 | 30 |
| TOTAL | 16 | 24 | 24 | 8 | 18 | 90 |

NA = Not Applicable.

REFERENCES

Angsubhakorn, S. et al., (1994) *Southeast Asian J. Trop. Med. Public Health* 25:554-59
Azzari, C. et al., (1987) *Pediatr. Med. Chir.* 9:391-6
Ballas, Z. J. et al., (2001) *J. Immunol.* 167:4878-86
Bancroft, W. H. et al., (1984) *Vaccine* 149:1005-10
Bakonyi et al., (2005) *Emerg. Inf. Dis.* 11:225
Banzhoff et al., (2003) *Gerentology* 49:177-84
Barr and Mitchell, *Immunology and Cell Biology* 74: 8-25 (1996)
Beasley, D. and Barrett A., (2002) *J. Virol.* 76:13097-13100
Beasley, D. et al., (2004) *Vaccine* 22:3722-26
Ben-Nathan et al., (2003) *J. Inf. Dis.* 188:5-12
Ben-Yehuda et al., (2003) *Vaccine* 21:3169-78
Bhamarapravati, N. et al., (1987) *Bull. World Health Organ.* 65:189-95
Bhamarapravati, N. and Sutee, Y. (2000) *Vaccine* Suppl 2:44-47
Brandt, E. E. (1990) *J. Infect. Dis.* 162:577-83
Bray, M. et al., (1996) *J. Virol.* 70:4162-66
Bray, M. and Lai, C. J. (1991) *Proc. Natl. Acad. Sci. USA* 88:10342-46
Falgout, B. et al., (1990) *J. Virol.* 64:4356-63
Fleeton, M. N. et al. (1990) *J. Gen. Virol.* 80:1189-98
Frech et al., (2005) *Vaccine* 23:946-50
Gibbons, R. V. and Vaughn, D. W. (2002) *British Medical Journal* 324:1563-66
Gluck, R. and Metcalf (2002) *Vaccine* 20:B10-6
Guebre-Xabier et al. (2004) *J. Virol.* 78:7610-18
Gubler, D. J. (1998) *Clin. Microbiol. Rev.* 11:480-96
Gupta, R. K. and G. R. Siber (1995) *Vaccine* 13:1263-76
Hall, R. A. et al., (1996) *J. Gen. Virol.* 77:1287-94
Halstead, S. B. (1988) *Science* 239:476-81
Hartmann, G. and Krieg, A. (2000) *J. Immunol.* 164:944-52
Hartmann, G. et al., (2000) *J. Immunol* 164:1617-24
Heinz, F. X. et al., (1983) *Virology* 130:485-501
Henchal, E. A. et al., (1985) *Am. J. Trop. Med. Hyg.* 34:162-69
Henchal, E. A. and Putnak J. R. (1990) *Clin. Microbiol Rev.* 3:376-96
Hoke, C. H. Jr. et al., (1990) *Am. J. Trop. Med. Hyg.* 43:219-26
Ivey-Hoyle, M. (1991) *Curr. Opin. Biotechnol.* 2:704-7
Jacobs, S. C. et al., (1994) *J. Gen. Virol.* 75:2399-2402

Jan, L. et al., (1993) *Am. J. Trop. Med. Hyg.* 48:412-23
Johansen, H. et al., (1989) *Genes Dev.* 3:882-89
Jones, T. A. and Kjeldgaard, M. (1998) *Essential O*, software manual, Uppsala
Kanesa-thasan, N. et al., (2001) *Vaccine* 19:3179-88
Katz, J. et al., (2004) *Immunol. Res.* 29:113-24.
Kensil, C. R. et al., (1991) *J. Immunol.* 146:431-37
Kimura-Kiroda, J. and K. Yasui (1988) *J. Immunol.* 141:3606-10
Klee et al., (2004) *Emerg. Inf. Dis.* 10:1405-11
Kreil et al., (1998) *J. Virol.* 72:3076-3081
Krieg, A. M. et al., (1995) *Nature* 374:546
Lai, C. J. et al., (1998) *Clin. Diagn. Virol.* 10:173-79
Laskowski, R. et al., (1993) *J. Appl. Cryst.* 26:283-91
Lawrence et al., (2003) *Commun. Dis. Intell.* 27:307-23
Leder et al., (2001) *Clin. Infect. Dis.* 33:1553-66
Leserman, L. (2004) *J. Liposome Res.* 14:175-89
Lieberman, M. M. and Frank, W. J. (1988) *J. Surg. Res.* 44:242
Lin and Wu (2003) *J. Virol.* 77:2600-6
Livingston, P. G. et al., (1995) *J. Immunol.* 154:1287-95
Lustig et al., (2000) *Viral Immunol.* 13:401-10
Mackenzie, J. M. et al., (1996) *Virology* 220:232-40
Mandl, C. W. (1989) *Virology* 6:564-571
Markoff, L. (2000) *Vaccine* 18:26-32
Mason, P. W. (1989) *J. Gen. Virol.* 70:2037-48
Mathew, A. et al. (1996) *J. Clin. Invest.* 98:1684-92
McDonell et al., U.S. Pat. No. 6,416,763
McElhaney (2003) *Conn. Med.* 67:469-74
McKee, K. T. et al., (1987) *Am. J. Trop. Med. Hyg.* 36:435-42
Men, R. et al., (1991) *J. Virol.* 65:1400-1407
Mishto, et al., (2003) *Ageing Res. Rev.* 2:419-32
Modis, Y. et al., (2003) *Proc. Natl. Acad. Sci. USA* 100:6986-91
Modis, Y. et al., (2004) *Nature* 427:313-9
Moingeon, P. (2002) *J. Biotechnol.* 98:189-98
Monath, T. et al., (2001) *Curr. Drug Targets Infect. Disord.* 1:37-50
Morbidity and Mortality Weekly Report (MMWR) (2003) vol. 52
Morbidity and Mortality Weekly Report (MMWR) (2004) vol. 53, Nov. 19, 2004
Morbidity and Mortality Weekly Report (MMWR) (2002) vol. 51:1-10
Murphy et al., (1986) *J. Clin. Microbiol.* 24:197-202
Newman, M. J. et al., (1992) *J. Immunol.* 148:2357-62
Otwinowski, Z. (1997) *Processing of X-ray Diffraction Data Collected in Oscillation Mode.* Academic Press, N.Y. Volume 276. pp 307-26
Oxenius, A. et al., (1999) *J. Virol.* 73:4120
Pawelec (2003) *Biogerontology* 4:167-70
Pawelec et al., (2002) *Front. Biosci.* 7:d1056-183
Platonov et al., (2001) *Emerg. Inf. Dis.* 7:128-32
Pletnev et al., (2002) *Proc. Natl. Acad. Sci. USA* 99:3036-41
Podda and Del Giudice (2003) *Expert Rev. Vaccines* 2:197-203
Prescrire Int. (2004) 13:206-8
Qiao et al., (2004) *J. Inf. Dis.* 190:2104-8
Ramon, G. (1925) *Bull. Soc. Centr. Med. Vet.* 101:227-34
Rey F. A., et al., (1995) *Nature* 375:291-98
Rodenhuis-Zybert et al., (2010) *PLos Pathogens* 6:1-9
Ruf et al., (2004) *Infection* 32:191-98
Review (2003) *Am. J. Trop. Med. Hyg.* 69 Supplement:1-60
Sabchareon, A. et al., (2002) *Am. J. Trop. Med. Hyg.* 66:264-72
Schlesinger, J. J. et al., (1985) *J. Immunol.* 135:2805-9
Schlesinger, J. J. et al., (1986) *J. Virol.* 60:1153-55
Schlesinger, J. J. et al., (1987) *J. Gen. Virol.* 68:853-57
Schlesinger, J. J. et al., (1990) *J. Gen. Virol.* 71:593-99
Schlesinger, J. J. et al., (1993) *Virology* 192:132
Smithburn et al., (1940) *Am. J. Trop. Med. Hyg.* 20:471-92
Smucny, J. et al., (1995) *Am. J. Trop. Med. Hyg.* 53:432-7
Tesh, R. B. et al., (2002) *Emerg. Inf. Dis.* 8:245-51
Tesh, R. B. et al., (2002) *Emerg. Inf. Dis.* 8:1392-7
Trirawatanapong, T. et al., (1992) *Gene* 116:139-150
Tsai et al., (1998) *Lancet* 352:767-71
Vaughn, D. W. et al., (1996) *Vaccine* 14:329-36
Verthelyi and Klinman (2003) *Clin. Immunol.* 109:64-71
Xiao, S-Y. et al., (2001) *Emerg. Infect. Dis.* 7:714-21
Wang et al., (2001) *J. Immunol.* 167:5273-77
Wang, S. et al. (2003) *Vaccine* 21:4297-4306
Weeratna, R. D. et al., (2000) *Vaccine* 18:1755-62
Windon, et al. (2001) *Vaccine* 20:490-97

What is claimed is:

1. A method for raising an immune response in a human patient, the method comprising administering a therapeutically effect amount of an immunogenic composition to the patient, wherein the immunogenic composition comprises an effective amount of purified dengue virus envelope ("E") protein monomers of serotype DEN-1, DEN-2, DEN-3, and DEN-4, a pharmaceutically acceptable excipient, and an effective amount of adjuvant; wherein the E proteins each constitute approximately 80% of the length of wild type E starting from amino acid residue 1 at its N-terminus, such that said E protein is secretable into growth medium when expressed recombinantly in a host cell; wherein the amount of DEN4 E protein is about 1.5 to about 3 times the individual amounts of DEN1, DEN2, and DEN3 E proteins, and wherein the composition induces the production of neutralizing antibodies in human subjects.

2. A method of producing neutralizing antibodies in a human subject against all four dengue serotypes comprising administering to the subject an effective amount of an immunogenic composition, wherein the immunogenic composition comprises an effective amount of purified dengue virus envelope ("E") protein monomers of serotype DEN-1, DEN-2, DEN-3, and DEN-4, a pharmaceutically acceptable excipient, and an effective amount of adjuvant; wherein the E proteins each constitute approximately 80% of the length of wild type E starting from amino acid residue 1 at its N-terminus, such that said E protein is secretable into growth medium when expressed recombinantly in a host cell; wherein the amount of DEN4 E protein is about 1.5 to about 3 times the individual amounts of DEN1, DEN2, and DEN3 E proteins, and wherein the composition induces the production of neutralizing antibodies the human subject against all four dengue serotypes.

3. The method of claim 1, wherein the amount of DEN4 protein is about twice the individual amount of DEN1, DEN2, and DEN3 proteins in the composition.

4. The method of claim 3, wherein the composition is administered via an intramuscular, subcutaneous or intradermal route of administration.

5. The method of claim 2, wherein the amount of DEN4 protein is about twice the individual amount of DEN1, DEN2, and DEN3 proteins in the composition.

6. The method of claim 5, wherein the composition is administered via an intramuscular, subcutaneous or intradermal route of administration.

7. The method of claim 1, wherein the composition induces the production of neutralizing antibodies in human subjects against DEN1, DEN2, DEN3, and DEN4 serotypes.

8. The method of claim 7, wherein the composition induces the production of balanced specific neutralizing antibodies in human subjects against DEN1, DEN2, DEN3, and DEN4 serotypes.

9. The method of claim 2, wherein the composition induces the production of balanced specific neutralizing antibodies in human subjects against DEN1, DEN2, DEN3, and DEN4 serotypes.

* * * * *

SEQUENCE LISTING

```
<160> NUMBER OF SEQ ID NOS: 10

<210> SEQ ID NO 1
<211> LENGTH: 1683
<212> TYPE: DNA
<213> ORGANISM: Dengue virus type 1

<400> SEQUENCE: 1
ttccatctga ccacacgagg gggagagccg cacatgatag ttagcaagca ggaaagagga      60
aagtcacttt tgtttaagac ctcagcaggt gtcaacatgt gcacccttat agcgatggat     120
ttgggagagt tatgtgagga cacaatgact tacaaatgcc ctcgaattac tgaggcgaaa     180
ccagatgacg ttgattgttg gtgcaatgct acagacacat gggtgaccta tggaacatgt     240
tcccaaactg gcgagcaccg acgggacaaa cgttccgtcg cactggcccc acacgtggga     300
cttggtttgg aaacaagaac cgaaacgtgg atgtcctctg aaggcgcttg gaaacagata     360
caaagagtgg agacttgggc cctgagacac ccaggattca cggtgatagc ccttttctca     420
gcacatgcca taggaacatc catcacccaa aaagggatta ttttcatttt gttaatgcta     480
```

```
gtaacaccat ccatggccat gcgatgcgtg ggaataggca gcagggactt cgtggaagga      540
ctgtcaggag caacttgggt agatgtggta ctggaacatg gaagttgcgt caccaccatg      600
gcaaaagaca aaccaacatt ggacattgaa ctcttgaaga cggaagtcac aaaccctgcc      660
gtcctgcgca aactgtgcat tgaagctaaa atatcaaaca ccaccaccga ttcaagatgt      720
ccaacacaag gagaagccac actggtggaa gaacaagacg gaactttgt gtgtcgacga      780 acgtttgtgg acagaggctg gggcaatggc tgtgggctct tcggaaaagg tagcctaata      840
acgtgtgcta agttcaagtg tgtgacaaaa ctggaaggaa agatagttca atacgaaaac      900
ttgaaatatt cagtaatagt caccgtccac actggagacc agcaccaggt gggaaatgaa      960
agcacagaac atgggacaac tgcaactata acacctcaag ctcctacgtc ggaaatacag     1020
ctgaccgact acgagctct acattggat tgctcaccta aacaggact ggactttaat     1080 gaaatggtgt tgttgacaat gaaagaaaaa tcatggctag tccacaaaca atggtttcta     1140
gacctaccac tgccttggac ctcgggagct tcaacatcac aagagacttg aacagacaa     1200 gatttgctgg taacattaa gacagcccat gcaaagaagc aggaagtagt cgtactagga     1260
tcacaagaag gagcaatgca cactgcgttg accggagcga cagaaatcca aacgtctgga     1320
acgacaacaa tttttgcagg acacctgaaa tgtagactaa aaatggacaa actgactcta     1380
aaagggatgt catatgttat gtgcacaggc tcattcaagc tagagaaaga agtggctgag     1440
acccagcatg gaaccgttct agtgcagatt aaatacgaag gaacagatgc accatgcaag     1500
atcccttttt cgacccaaga tgaaagagga gtaacccaga acgggagatt aataacagcc     1560
aaccctatag ttactgacaa agaaaaacca gtcaacattg aggcagaacc gccttttggt     1620
gagagttaca tcgtgatagg agcaggtgaa aaagctttga actaagctg gttcaagaag     1680 gga                                                                   1683

<210> SEQ ID NO 2
<211> LENGTH: 1683
<212> TYPE: DNA
<213> ORGANISM: Dengue virus type 2

<400> SEQUENCE: 2
tttcatctga ccacacgcaa cggagaacca cacatgatcg tcagtagaca agaaaaaggg       60
aaaagccttc tgtttaagac aaaggacggc acgaacatgt gtaccctcat ggccatggac      120
cttggtgagt tgtgtgaaga cacaatcacg tataaatgtc cctttctcaa gcagaacgaa      180
ccagaagaca tagattgttg gtgcaactcc acgtccacat gggtaactta tgggacatgt      240
accaccacag gagagcacag aagagaaaaa agatcagtgg cgcttgttcc acacgtggga      300
atgggattgg agacacgaac tgaaacatgg atgtcatcag aagggcctg gaaacatgcc      360 cagagaattg aaacttggat tctgagacat ccaggcttta ccataatggc cgcaatcctg      420
gcatacacca taggaacgac gcatttccaa agagtcctga tattcatcct actgacagcc      480 atcgctccctt caatgacaat gcgctgcata ggaatatcaa ataggacttt gtggaagga      540 gtgtcaggag ggagttgggt tgacatagtt ttagaacatg gaagttgtgt gacgacgatg      600 gcaaaaata aaccaacact ggacttgaa ctgataaaaa cagaagccaa acaacccgcc      660
accttaagga agtactgtat agaggctaaa ctgaccaaca cgacaacaga ctcgcgctgc      720
ccaacacaag gggaacccac cctgaatgaa gagcaggaca aaggtttgt ctgcaaacat      780 tccatggtag acagaggatg gggaaatgga tgtggattat ttggaaaagg aggcatcgtg      840
acctgtgcca tgttcacatg caaaaagaac atggaggaaa aaattgtgca gccagaaaac      900
```

```
ctggaataca ctgtcgttat aacacctcat tcaggggaag aacatgcagt cggaaatgac    960
acaggaaaac atggtaaaga agtcaagata acaccacaga gctccatcac agaggcggaa   1020
ctgacaggct atggcactgt tacgatggag tgctctccaa gaacgggcct cgacttcaat   1080
gagatggtgt tgctgcaaat gaaagacaaa gcttggctgg tgcacagaca atggttccta   1140
gacctaccgt tgccatggct gcccggagca gacacacaag gatcaaattg gatacagaaa   1200
gagacactgg tcaccttcaa aaatccccat gcgaaaaaac aggatgttgt tgtcttagga   1260
tcccaagagg gggccatgca tacagcactc acaggggcta cggaaatcca gatgtcatca   1320
ggaaacctgc tgttcacagg acatcttaag tgcaggctga atgacaa attacaactt   1380 aaagggatgt catactccat gtgcacagga aagtttaaag ttgtgaagga aatagcagaa   1440
acacaacatg gaacaatagt cattagagta caatatgaag gagacggctc tccatgcaag   1500
atcccttttg agataatgga tctggaaaaa agacatgttt gggccgcct gatcacagtc   1560 aatccaattg taacagaaaa ggacagccca gtcaacatag aagcagaacc tccattcgga   1620
gacagctaca tcatcatagg agtggaacca ggacaattga agctggactg gttcaagaaa   1680
gga                                                                 1683
```

<210> SEQ ID NO 3
<211> LENGTH: 1677
<212> TYPE: DNA
<213> ORGANISM: Dengue virus type 3

<400> SEQUENCE: 3

```
ttccacttga cttcacgcga tggagagccg cgcatgattg tggggaagaa tgaaagaggg     60
aaatccctac tttttaagac agcttctgga atcaacatgt gcacactcat agccatggac   120
ttgggagaga tgtgtgatga cacggtcact tacaaatgcc cccacattgc cgaagtggaa   180
cctgaagaca ttgactgctg gtgcaacctt acatcgacat gggtgactta tggaacgtgc   240
aatcaagctg gggagcacag acgcgacaag agatcagtgg cgttagctcc ccatgtcggc   300
atgggactgg acacacgcac ccaaaacctgg atgtcggctg aaggagcctg agacaagtc   360 gagaaggtag agacatgggc ccttaggcac ccagggttca ccatactagc tctatttctt   420
gcccattaca taggcacttc cttgacccag aaagtggtta ttttatact actaatactg   480 gtcactccat ccatggcaat gagatgcgtg ggagtaggaa acagagattt tgtggaaggt   540
ctatcgggag ctacgtgggt tgacgtggtg ctcgagcacg gtgggtgtgt gaccaccatg   600
gctaagaaca agcccacgct ggacatagag cttcagaaga ccgaggccac ccaactggcg   660
accctaagga gttatgcat tgagggaaaa attaccaaca taacaactga ctcaaggtgt   720
cctacccagg gggaagcgat tttacctgag agcaggacc agaactacgt atgtaagcat   780
acatacgtgg atagaggctg gggaaacggt tgtggttttgt ttggaaaagg aagcttggtg   840
acatgcgcga aatttcaatg cttagaatca atagagggaa aagtggtgca acatgagaac   900
ctcaaataca ctgtcatcat tacagtgcac acaggagacc aacaccaggt gggaaatgaa   960
acgcagggag tcacggctga gataacaccc caggcatcaa ccgttgaagc tatcttgcct   1020
gaatatggaa cccttgggct agaatgctca ccacggacag gtttggattt caatgaaatg   1080
atcttattga caatgaagaa caaagcatgg atggtacata acaatggtt ctttgaccta   1140 cccctaccat ggcatcagg agctacaaca gagacaccaa cttggaacag gaagagcttt   1200
cttgtgacat tcaaaaatgc acatgcaaaa aagcaagaag tagttgtcct tggatcgcaa   1260
```

```
gagggagcaa tgcacacagc gctgacagga gctacagaga tccaaaactc aggaggcaca      1320
agcatttttg cggggcactt gaaatgtaga cttaagatgg acaaattgga actcaagggg      1380
atgagctatg caatgtgctt gaacaccttt gtgttgaaga aagaagtctc cgagacgcag      1440
catgggacaa tactcattaa ggttgagtac aaagggaag atgcaccttg caagattcct       1500
ttctccacgg aggatggaca agggaaagct cacaatggta gactgatcac agccaaccca     1560
gtggtgacca agaaggagga gcctgtcaac attgaggctg aacctccttt tggggaaagt      1620
aacatagtga ttggaattgg agacaaagcc ttgaaaatta actggtacaa gaaggga        1677
```

<210> SEQ ID NO 4
<211> LENGTH: 1683
<212> TYPE: DNA
<213> ORGANISM: Dengue virus type 4

<400> SEQUENCE: 4

```
tttcacttgt caacaagaga tggcgaaccc cttatgatag tggcaaaaca cgaaaggggg      60
agacctctct tgtttaagac aacagaggga atcaacaaat gcactcttat tgccatggac      120
ctgggtgaaa tgtgtgagga caccgtcacg tatgaatgcc ctctactggt caataccgaa      180
cctgaggaca ttgattgctg gtgcaatctc acgtctgcct gggtcatgta tgggacatgc      240
actcagagtg gggaacggag acgggagaag cgctcagtag ccctaacacc acattcagga     300
atgggattgg agacaaggc tgagacatgg atgtcatcgg aaggggcttg gaaacatgct      360
cagagggtag agagttggat actcagaaac ccaggattcg ctctcttggc aggatttatg     420
gcctatatga ttgggcaaac aggaatccag cgaacagtct tctttgttct aatgatgctg     480
gtcgccccat cctacggaat gcgatgcgtg ggagtgggga acagagactt tgtggaagga    540
gtctcaggtg gagcatgggt cgatttggtg ctagaacatg gaggatgtgt cacaaccatg    600
gcccagggaa aaccaacctt ggattttgaa ctgatcaaga acagccaa ggaagtggct       660 ctgttaagaa cctattgcat tgaagcctcg atatcaaaca taaccacggc aacaagatgt    720
ccaacgcaag gagaaccta tctcaaagag gaacaagatc aacagtacat tgccggaga     780 gatgtggtag acagagggtg gggcaatggc tgtggcttgt ttgggaaagg aggagttgtg    840
acatgtgcga gttttcatg ctcggggaag ataacaggca atttggtcca aattgagaac    900
cttgaataca cagtagttgt aacagtccac aatggagaca cccatgcagt aggaaatgac    960
acatccaacc atggagtgac agccacgata ccccccaggt caccatcggt agaagttaaa    1020
ttaccggatt atggagaatt aacactcgat tgtgaacca ggtccggaat tgattttaat      1080
gagatgattc tgatgaaaat gaaaagaaaa acgtggcttg tgcacaagca atggtttttg     1140
gatctacctc taccatgggc agcaggagca gacacatcag aagttcattg gaattacaaa    1200
gagagaatgg tgacattcaa ggttcctcat gccaagagac aggatgtgac agtgctagga    1260
tctcaggaag gagccatgca ttctgccctc accggagcta cagaagtgga ttccggtgat    1320
ggaaaccaca tgtatgcagg acatctgaaa tgcaaagttc gcatggagaa attgagaatt     1380
aagggaatgt catacacgat gtgctcagga aagttctcaa ttgacaaaga gatggcagaa    1440
acacagcatg gacaacagt ggtaaaagtc aagtatgagg gtgctggagc tccatgtaaa     1500
gttcccatag agataagaga tgtgaacaag gaaaagtgg tagggcgcat catctcatct     1560 acccctttg ctgagtatac caacagtgta accaacatag aattagaacc cccctttggg     1620
gacagctaca tagtaatagg tgttggagac agtgcattaa cactccattg gttcaggaaa    1680
ggg                                                                    1683
```

<210> SEQ ID NO 5
<211> LENGTH: 1851
<212> TYPE: DNA
<213> ORGANISM: Artificial Sequence
<220> FEATURE:
<223> OTHER INFORMATION: DEN4 prM-80E linked to sequence encoding dimerization domain

<400> SEQUENCE: 5

```
tttcacttgt caacaagaga tggcgaaccc cttatgatag tggcaaaaca cgaaaggggg      60
agacctctct tgtttaagac aacagaggga atcaacaaat gcactcttat tgccatggac     120
ctgggtgaaa tgtgtgagga caccgtcacg tatgaatgcc ctctactggt caataccgaa     180
cctgaggaca ttgattgctg gtgcaatctc acgtctgcct gggtcatgta tgggacatgc     240
actcagagtg gggaacggag acgggagaag cgctcagtag ccctaacacc acattcagga    300
atgggattgg agacaaggge tgagacatgg atgtcatcgg aagggg cttg gaaacatgct     360
cagagggtag agagttggat actcagaaac ccaggattcg ctctcttggc aggatttatg     420
gcctatatga ttgggcaaac aggaatccag cgaacagtct tctttgttct aatgatgctg     480
gtcgcccat cctacggaat gcgatgcgtg ggagtgggga cagagactt tgtggaagga     540
gtctcaggtg gagcatgggt cgatttggtg ctagaacatg gaggatgtgt cacaaccatg     600
gcccaggaa aaccaacctt ggattttgaa ctgatcaaga acagccaa ggaagtggct     660
ctgttaagaa cctattgcat tgaagcctcg atatcaaaca taaccacggc aacaagatgt     720
ccaacgcaag gagaacctta tctcaaagag gaacaagatc aacagtacat ttgccggaga    780
gatgtggtag acagagggtg gggcaatggc tgtggcttgt ttgggaaagg aggagttgtg     840
acatgtgcga gtttctcatg ctcggggaag ataacaggca ttggtcca aattgagaac     900
cttgaataca cagtagttgt aacagtccac aatggagaca cccatgcagt aggaaatgac     960
acatccaacc atggagtgac agccacgata accccaggt caccatcggt agaagttaaa    1020
ttaccggatt atggagaatt aacactcgat tgtgaaccca ggtccggaat tgatttaat    1080
gagatgattc tgatgaaat gaaaagaaa acgtggcttg tgcacaagca atggttttg     1140
gatctacctc taccatgggc agcaggagca gacacatcag aagttcattg gaattacaaa    1200
gagagaatgg tgacattcaa ggttcctcat gccaagagac aggatgtgac agtgctagga    1260
tctcaggaag gagccatgca ttctgccctc accggagcta cagaagtgga ttccggtgat    1320
ggaaaccaca tgtatgcagg acatctgaaa tgcaaagttc gcatggagaa attgagaatt    1380
aagggaatgt catacacgat gtgctcagga aagttctcaa ttgacaaaga gatggcagaa    1440
acacagcatg gacaacagt ggtaaaagtc aagtatgagg gtgctggagc tccatgtaaa    1500
gttcccatag agataagaga tgtgaacaag gaaaaagtgg tagggcgcat catctcatct    1560
accccttttg ctgagtatac caacagtgta ccaacatag aattagaacc ccccttggg    1620
gacagctaca tagtaatagg tgttggagac agtgcattaa cactccattg gttcaggaaa    1680
gggggtggtg gttctggtgg tggtggtacc ggcggtggct ccggcggtgg ctcccccgc    1740
atgaagcagc tggaggacaa ggtggaggag ctgctgtcca agaactacca cctggagaac    1800
gaggtggccc gcctgaagaa gctggtgggc gagcgcggcg gttgcggcgg t          1851
```

<210> SEQ ID NO 6
<211> LENGTH: 395
<212> TYPE: PRT
<213> ORGANISM: Dengue virus type 1

<400> SEQUENCE: 6

Met Arg Cys Val Gly Ile Gly Ser Arg Asp Phe Val Glu Gly Leu Ser
1               5                   10                  15

Gly Ala Thr Trp Val Asp Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Ile Lys Tyr Glu Gly Thr Asp Ala Pro Cys Lys Ile Pro
                325                 330                 335

Phe Ser Thr Gln Asp Glu Arg Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Ile Gly Ala Gly Glu
    370                 375                 380

Lys Ala Leu Lys Leu Ser Trp Phe Lys Lys Gly
385                 390                 395

```
<210> SEQ ID NO 7
<211> LENGTH: 395
<212> TYPE: PRT
<213> ORGANISM: Dengue virus type 2

<400> SEQUENCE: 7
```

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Asp Ser Arg Cys Pro Thr Gln Gly Glu Pro
65                  70                  75                  80

Thr Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Ile Val Gln Pro Glu Asn Leu Glu Tyr Thr Val Ile Thr Pro His
    130                 135                 140

Ser Gly Glu Glu His Ala Val Gly Asn Asp Thr Gly Lys His Gly Lys
145                 150                 155                 160

Glu Val Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Lys Asp Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asp Trp Phe Lys Lys Gly
385                 390                 395

<210> SEQ ID NO 8
<211> LENGTH: 393
<212> TYPE: PRT
<213> ORGANISM: Dengue virus type 3

<400> SEQUENCE: 8

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Ser Ile Glu Gly Lys
        115                 120                 125

Val Val Gln His Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Val Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Leu Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Lys Ala
        370                 375                 380

```
                340                 345                 350
Ser Ser Thr Pro Phe Ala Glu Tyr Thr Asn Ser Val Thr Asn Ile Glu
        355                 360                 365

Leu Glu Pro Pro Phe Gly Asp Ser Tyr Ile Val Ile Gly Val Gly Asp
        370                 375                 380

Ser Ala Leu Thr Leu His Trp Phe Arg Lys Gly
385                 390                 395

<210> SEQ ID NO 10
<211> LENGTH: 451
<212> TYPE: PRT
<213> ORGANISM: Artificial Sequence
<220> FEATURE:
<223> OTHER INFORMATION: DEN4-80E linked to dimerization domain

<400> SEQUENCE: 10

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20

-continued

```
            305                 310                 315                 320
Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
                340                 345                 350

Ser Ser Thr Pro Phe Ala Glu Tyr Thr Asn Ser Val Thr Asn Ile Glu
                355                 360                 365

Leu Glu Pro Pro Phe Gly Asp Ser Tyr Ile Val Ile Gly Val Gly Asp
            370                 375                 380

Ser Ala Leu Thr Leu His Trp Phe Arg Lys Gly Gly Gly Gly Ser Gly
385                 390                 395                 400

Gly Gly Gly Thr Gly Gly Gly Ser Gly Gly Gly Ser Pro Arg Met Lys
                405                 410                 415

Gln Leu Glu Asp Lys Val Glu Glu Leu Leu Ser Lys Asn Tyr His Leu
                420                 425                 430

Glu Asn Glu Val Ala Arg Leu Lys Lys Leu Val Gly Glu Arg Gly Gly
                435                 440                 445

Cys Gly Gly
    450
```